United States Patent
Nigam et al.

(10) Patent No.: US 11,238,722 B2
(45) Date of Patent: *Feb. 1, 2022

(54) METHODS AND SYSTEMS FOR PROVIDING ONLINE MONITORING OF RELEASED CRIMINALS BY LAW ENFORCEMENT

(71) Applicant: Optimum ID, LLC, Cleveland, OH (US)

(72) Inventors: Hemanshu Nigam, Oak Park, CA (US); Michael Lang, Phoenix, AZ (US); James Drolshagen, Wheaton, IL (US)

(73) Assignee: OPTIMUM ID LLC, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/653,667

(22) Filed: Oct. 15, 2019

(65) Prior Publication Data

US 2020/0043319 A1 Feb. 6, 2020

Related U.S. Application Data

(63) Continuation of application No. 16/283,602, filed on Feb. 22, 2019, now abandoned, which is a continuation of application No. 16/019,192, filed on Jun. 26, 2018, now abandoned, which is a continuation of application No. 15/239,797, filed on Aug. 17, 2016, now Pat. No. 10,008,099.

(60) Provisional application No. 62/205,824, filed on Aug. 17, 2015, provisional application No. 62/330,846, filed on May 3, 2016.

(51) Int. Cl.
*G08B 25/00* (2006.01)
*G06F 16/51* (2019.01)
*G06F 16/583* (2019.01)
*A61B 5/117* (2016.01)
*G06F 16/58* (2019.01)
*G06K 9/00* (2006.01)
*G06Q 50/26* (2012.01)

(52) U.S. Cl.
CPC ............ *G08B 25/001* (2013.01); *A61B 5/117* (2013.01); *G06F 16/51* (2019.01); *G06F 16/5838* (2019.01); *G06F 16/5866* (2019.01); *G06K 9/00228* (2013.01); *G06K 9/00288* (2013.01); *G06K 9/00892* (2013.01); *G06K 9/00912* (2013.01); *G06K 9/00899* (2013.01); *G06Q 50/26* (2013.01)

(58) Field of Classification Search
CPC ... G08B 25/001; G06F 16/5838; G06F 16/51; G06F 16/5866; A61B 5/117; G06K 9/00228; G06K 9/00892; G06K 9/00912; G06K 9/00288; G06K 9/00899; G06Q 50/26; H04W 4/02
USPC ...................................... 340/573.4
See application file for complete search history.

(56) References Cited

U.S. PATENT DOCUMENTS 8,724,908 B2 * 5/2014 Dale .................... G06K 9/6254
  382/224
9,235,733 B2 * 1/2016 Birdwell .................. G06K 5/00
(Continued)

*Primary Examiner* — John A Tweel, Jr.

(57) ABSTRACT

The methods and systems are designed to utilize an integrated combination of just in time, just in place, and just on device actions connected to an image recognition process for monitoring criminals who are probation, offenders who are on parole, sex offenders, and witnesses under protection by law enforcement.

20 Claims, 15 Drawing Sheets

(56) References Cited

U.S. PATENT DOCUMENTS

| | | | |
|---|---|---|---|
| 10,008,099 B2* | 6/2018 | Drolshagen | G06F 16/5866 |
| 10,225,248 B2* | 3/2019 | Nigram | H04L 63/0861 |
| 2006/0050932 A1* | 3/2006 | Tumey | G06K 9/00087 |
| | | | 382/116 |
| 2009/0164796 A1* | 6/2009 | Peirce | G06F 21/32 |
| | | | 713/186 |
| 2012/0075442 A1* | 3/2012 | Vujic | G07C 9/257 |
| | | | 348/61 |
| 2014/0289833 A1* | 9/2014 | Briceno | H04L 63/08 |
| | | | 726/7 |
| 2014/0294257 A1* | 10/2014 | Tussy | G06Q 10/00 |
| | | | 382/118 |
| 2015/0271777 A1* | 9/2015 | Torgersrud | H04W 12/06 |
| | | | 455/456.3 |

\* cited by examiner

METHODS AND SYSTEMS FOR PROVIDING ONLINE MONITORING OF RELEASED CRIMINALS BY LAW ENFORCEMENT

CROSS-RELATED APPLICATIONS

This application is a continuation of U.S. patent application Ser. No. 16/283,602, filed Feb. 22, 2019, which is a continuation of U.S. patent application Ser. No. 16/019,192, filed Jun. 26, 2018, which is a continuation of U.S. patent application Ser. No. 15/239,797, filed Aug. 17, 2016, issued as U.S. Pat. No. 10,00,899 on Jun. 26, 2018, which claims priority to and the benefit of U.S. Provisional Patent Application Ser. No. 62/205,824, filed Aug. 17, 2015, all of which are incorporated by reference. This application benefits and claims priority to U.S. Provisional Patent Application Ser. No. 62/330,846, filed May 3, 2016, which is incorporated by reference.

BACKGROUND

For decades, individuals under house arrest or parole have been required to wear an ankle monitor (also known as a tether, or ankle bracelet), which is a homing device that sends a radio frequency signal containing location and other information to a receiver, at timed intervals. If an offender moves outside of an allowed range, law enforcement is notified. Ankle monitors are designed to be tamper-resistant and can alert law enforcement to removal attempts.

Many believe that requiring a criminal, who has been released from prison, to wear a GPS bracelet, is essential for law enforcement to keep track of such individuals, and is a tool for the prevention repeat crimes from being committed. Accordingly, some states have passed laws, which required round-the-clock GPS monitoring of serious sex offenders for life.

Typically, the GPS systems involve an ankle monitor designed to stay within a specified distance of a GPS transmitter, which is in communication with a satellite that then transmits location information over cellular networks to a central computer. Such systems are designed to send an alert if an offender tries to remove the device or enter a forbidden area, such as, for example, a school or park, a liquor store, or near a victim's residence. However, the alerts go out for a variety of routine reasons, such as, for example, GPS signals blocked by buildings, dead batteries, cracked cases, loose straps, which can overwhelm law enforcement with volumes of false positives. Since, many technological problems exist with current GPS monitoring systems, new methods and systems for providing online monitoring of released criminals are needed.

SUMMARY

Various embodiments provide methods and systems for providing online verification and monitoring of released criminals. The methods and systems are designed to utilize an integrated combination of just in time, just in place, and just on device actions connected to an image recognition process for monitoring criminals who are probation, offenders who are on parole, sex offenders, and witnesses under protection by law enforcement.

DRAWINGS

The present disclosure will become more fully understood from the description and the accompanying drawings, wherein.

Figure 1:
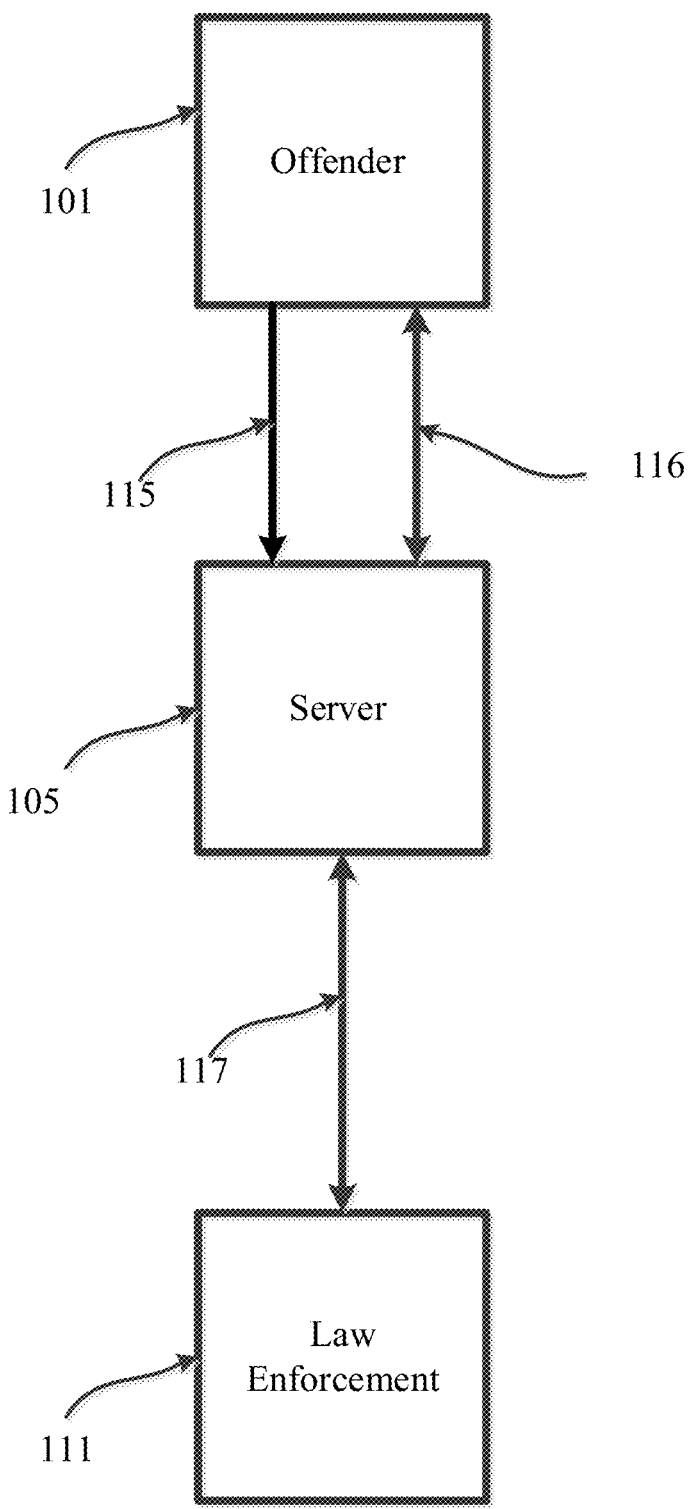
FIG. 1 is a block diagram illustrating an exemplary system for monitoring released criminals, in accordance to various embodiments.

The drawings described herein are for illustrative purposes only of selected embodiments and not all possible implementations, and are not intended to limit the scope of any of the exemplary embodiments disclosed herein or any equivalents thereof. It is understood that the drawings are not drawn to scale. For purposes of clarity, the same reference numbers will be used in the drawings to identify similar elements.

DESCRIPTION

The following description is merely exemplary in nature and is in no way intended to limit the exemplary embodiments, their application, or uses. It should be understood that steps within a method may be executed in different order without altering the principles of the present disclosure. For example, various embodiments may be described herein in terms of various functional components and processing steps. It should be appreciated that such components and steps may be realized by any number of hardware components configured to perform the specified functions.

Various embodiments provide methods and systems for providing online verification and security. Some embodiments include methods for providing a secured system. Various methods and systems, described herein, can be a mobile application, which improves security throughout a whole range of internet-related activities.

In some embodiments, methods and systems, described herein, improve security for online or internet-related activities in at least three ways. First, individual offenders are provided the means to prove their identity on the Internet through a proprietary process of ID verification in time, place, and device. Second, Internet providers are provided the means to verify that their own offenders are using their real identities, and that the person who currently is using their service is indeed that verified individual. Third, the public is provided the means to ensure that they are not being misled, harassed, or threatened by anonymous or fraudulent Internet miscreants.

The methods and systems are designed to utilize an integrated combination of just in time, just in place, and just on device actions connected to an image recognition process to reduce or remove the risk of an Offender utilizing fake or stolen credentials in order to get verified.

For example, a method of identification verification can include accessing the verification application on a mobile device and completing a registration process. The verification application can be interfaced with a verification engine on webserver, which is communication with the mobile device. In some cases, it may appear to the Offender that the verification application is doing an analysis to determine an outcome, but the analysis is actually being run by the verification engine. First, the Offender is instructed to take a picture or a short video of him/her with their mobile device ("Offender photo"). The Offender can be allowed to repeat this process until the Offender is satisfied with the image. The Offender is then given a limited number of minutes to take a photograph of their government identification card ("ID Card photo"), such as, for example, a driver's license, a state ID card, a passport, a school ID, or any such identification device, which has a photograph of the Offender.

In addition, the verification application can verify that the ID Info is valid via a comparison with the appropriate governmental records. For certain applications, the verification application can verify that the ID Info is not on the National Sexual Predator List or similar sexual predator database.

In some embodiments, secondary verification data can be collected and connected to the token. The verification application can prompt the Offender to read a couple of sentences into their mobile device, which is recorded by the verification application. This recording can be stored for use in voice-recognition applications. For example, the verification application may ask the Offender to apply a thumbprint and/or fingerprint to an interface on their mobile device. The thumbprint and/or fingerprint is recorded as a secondary verification data and stored for use in fingerprint-recognition applications. In other example, the verification application may ask the Offender to an image of the Offender's retina. The retina image is recorded as a secondary verification data and stored for use in image-recognition applications. From time to time the Offender may be asked to renew their Verification status by completing the above process again.

In some embodiments the verification application may request of proof from the Offender that the person using the device is actually the Offender. This request may be generated on a prescribed time period or randomly. This request may be generated when the application identifies that the GPS of the device is outside a boundary. The boundary can be changed by the Offender.

For example, the form of proof can be a request for the Offender to take a new Offender photo, which is submitted and compared, using the facial-recognition routine, to Offender photo(s) and ID Card photo(s) in the Offender Profile. For example, the form of proof can be a request for the Offender to read a few words aloud into the verification application, which is submitted and compared, using a voice-recognition routine, to previously recorded Offender's voice in the Offender Profile. For example, the form of proof can be a request for the Offender to apply a fingerprint and/or a thumbprint or both to an interface on their mobile device, which is submitted and compared, using a fingerprint-recognition routine to the fingerprint and/or thumbprint of Offender in the Offender Profile. For example, the form of proof can be a request for the Offender to take an image of the eye retina, which is submitted and compared to the image of the eye retina of the Offender in the Offender Profile.

Law enforcement can connect with verification system ("Verie") through a secure API, which provides the law enforcement with the means to deliver verification technology to their end offenders' smartphones. After verifying an offender's identity, the verification system can quickly re-verify an offender anytime, anyplace.

Some embodiments provide a verification engine, which is an identity verification technology solution. By combining a proprietary smartphone-based identification application with an enterprise API, the verification engine allows law enforcement to verify that an online individual is truly who they say they are. The verification engine can confirm that a person's online identity is real, and that it belongs to the person who is claiming it. The verification engine can identify the physical location of the individual. The verification engine establishes an identification, which cannot be duplicated, because it is uniquely tied to the individual's smartphone.

In some embodiments, the GPS coordinates can include the angle the photo was taken using the gyroscope in the device. In some aspects of these embodiments, a first photo of the ID Card is taken at a first angle and a second photo of the ID Card is taken at a second angle. The first angle and the second angle can be recorded by the device and tagged to the photos. A holograph or an embossed symbol may be identified on the ID Card by using the angle of the first photo and the angle of the second photo.

In some embodiments, the Offender photo and the ID Card photo must be taken within a defined time period. For example, the Offender photo and the ID Card must be taken within a one-minute time period. This time period can be varied depending on the application. The GPS coordinates tagged to the Offender photo and tagged to the ID Card photo must be within a defined distance. For example, the GPS coordinates tagged to the Offender photo and tagged to the ID Card photo must be within 20 feet. In another example, the GPS coordinates tagged to the Offender photo and tagged to the ID Card photo must be within 3 feet. The defined distance of the GPS coordinates can be varied depending on the application; however, this distance must be greater than the margin of error of the GPS based on the capabilities of the device and the accuracy of the satellites used by the GPS.

Some embodiments provide a method for providing a secured system. The method can include the steps of: generating an image of a face of an offender at first location with a device comprising a clock and a GPS; tagging the image with GPS coordinates of the first location; tagging the image with a time and a date of the generating of the image; generating an image of an identification card comprising a picture of the offender at a second location; tagging the image of the identification card with GPS coordinates of the second location; and tagging the image of an identification card with a time and date of the generating of the image of the identification card.

The method can further include the steps of: comparing the image of the face and the image of the picture of the offender; determining the likelihood that the image of the face and the image of the picture of the offender are substantially the same; determining if the GPS coordinates of the first location and the GPS of the second location are substantially the same; determining if the time and date of the generating the image of face and the time and date of the generating the image of the identification card are within a defined time window. One or more of these steps can be carried out by a verification engine on a web server.

The method can include the steps of receiving and storing an initial secondary identifier after the generating the authorization key; requesting offender to input a secondary identifier at a later time; receiving the secondary identifier from the offender; comparing the secondary identifier to the initial secondary identifier; determining if the secondary identifier and the initial secondary identifier are substantially the same; and renew the authorization key if the secondary identifier and the initial secondary identifier are substantially the same.

The secondary identifier can be one of: a voice pattern generated by the offender and captured by a microphone on the device; an image of a retina of an offender's eye captured by the device; at least one fingerprint of the offender captured by the device; a palm scan of the offender captured by the device; a photo of the offender captured by the device; a RFID tag tethered to the device; and a password.

Some embodiments provide a system for secured transactions over a network. The system can include an app, which is downloadable to a device, a verification engine on a server at the location on the network, and a verification token configured to allow the offender access to at least one restricted website.

The device can be a smart phone or tablet, however, the device has at least a camera, a GPS locator, a network interface, and an offender interface (such as, for example, an offender app).

In some configurations, the app includes: a process to initiate an offender to take and capture a picture of an offender's face with the camera; a process to capture a first set of GPS coordinates, a first time, and a date of the picture of the offender's face; a process to initiate the offender to take and capture a picture of an identification card with the camera; a process to capture a second set of GPS coordinates, a second time, and a date of the picture of the identification card; a process to capture identification data of the device; a process to send data comprising at least one of the picture of the offender's face, the picture of the identification card, the first set of GPS coordinates, the second set of GPS coordinates, the time and date of the picture of the offender's face, the time and date of the picture of the identification card, and the identification data to a location on the network; and a process to receive and communicate information.

In some configurations, the verification engine includes: an input configured to receive the data from the app; an image comparison algorithm configured to compare the picture of the offender's face, the picture of the identification card, then determine the likelihood that the offender and a person in the picture of the identification card are substantially the same; a location comparison algorithm configured to determine if the first set of GPS coordinates and the second set of GPS coordinates are substantially the same; and a time comparison algorithm configured to determine if the time and date of the picture of the offender's face, the time and date of the picture of the identification card are substantially the same.

In some configurations, the system includes a verification message configured to be send to the app if the offender and a person in the picture of the identification card are substantially the same, if the first set of GPS coordinates and the second set of GPS coordinates are substantially the same, and if the time and date of the picture of the offender's face, the time and date of the picture of the identification card are substantially the same.

In some aspects, the system includes a not verified message configured to be sent to the app if at least one of an outcome of the image comparison algorithm is negative, or if an outcome of the location comparison algorithm is negative, or if an outcome of the time comparison is negative.

The system can include a secondary verification system. The secondary verification system can be configured to: receive and store an initial secondary identifier at a first time; receive a second secondary identifier at a second time; compare the second secondary identifier to the initial secondary identifier; determine if the second secondary identifier and the initial secondary identifier are substantially the same; and renew the verification token if the second secondary identifier and the initial secondary identifier are substantially the same.

The secondary identifier can be an image of a retina of an offender's eye captured by the camera. The secondary identifier can be at least one fingerprint of the offender captured by the device. The secondary identifier can be a voice pattern generated by the offender and captured by a microphone on the device.

Turning to FIG. 1, a block diagram illustrates an exemplary system for monitoring released criminals, in accordance to various embodiments. An offender 101 using a device, such as a smartphone, communicates with an agent from law enforcement 111 through a server 105 running methodology for providing online monitoring and verification of released criminals. The law enforcement communicates with server through a secure API 117, which provides the agent the means to deliver the methodology to the offender's device.

Once an app is installed on the offender's device, the offender 101 is led through a process for enrollment 115 in the online monitoring and verification program. The enrollment process includes entering personal information, a PIN, and at least one selfie image taken by the device. The enrollment 115 can be conducted at the agent's office, who can verify that the person being enrolled is the actual offender 101. However, the enrollment 115 can be conducted off-site, which can include the entering of an image of an approved identification card, as well as, the GPS coordinates of location that the offender 101 is going through the enrollment 115.

Verification 116 is initiated by the law enforcement 111 either automatically or manually. The offender 101 has a limited amount of time, which is indicated on the device, to response to verification 116. The offender 101 takes a new selfie in real time and send the image of the selfie to the law enforcement 111 to complete verification 116. The verification 116 can provide additional information for the offender's device, such as the device ID and/or GPS coordinates of the location of where the offender 101 completed verification 116. The verification 116 can include a requirement to provide at least one secondary identifier from the offender 101 to complete verification 116.

Figure 2:
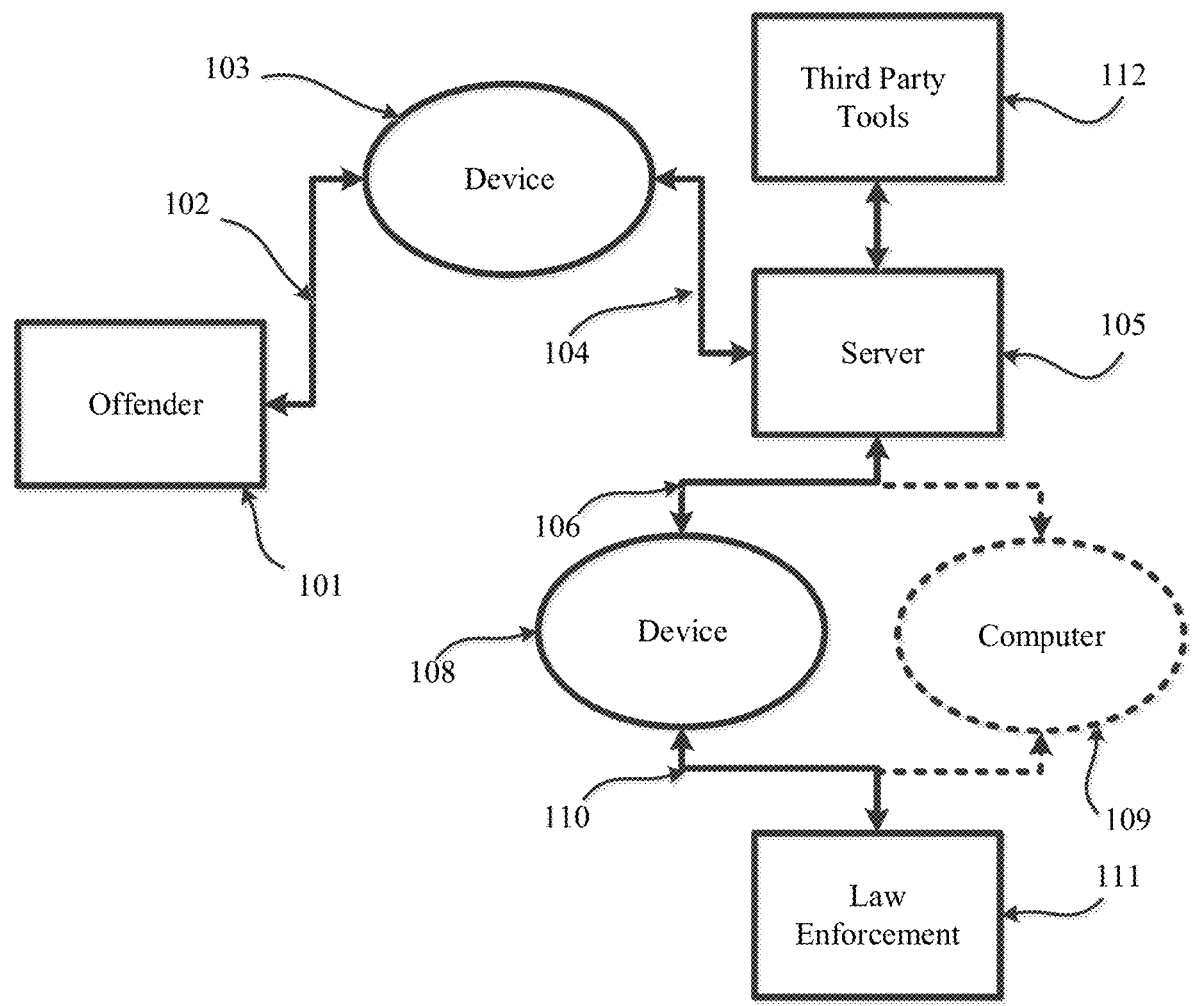
FIG. 2 is a flowchart illustrating various elements for providing the online verification methods and systems, in accordance with various embodiments.

Now with reference to FIG. 2, a flowchart illustrates various elements for providing the online verification methods and systems. The offender 101 operates the device 103 via offender interface 102. The device 103 can be any device with an offender interface 102, an image capture mechanism, and web capabilities. An image capture mechanism can be a digital device, a mechanical device, or a combination of both. The web capabilities can be a Wi-Fi interface, a Bluetooth interface, a mobile service interface, or any other such system or device, now known or developed in the future. Examples of the device 103 can include smartphones, tablets, and other such devices. For example, the device 103 can be an iPhone, an iPad, an apple watch, and other such devices. Examples of the device 103 can include phones and tablets, which operate on android operating systems. Other examples of the device 103 can include phones and tablet, which operate on Microsoft operating systems. In some aspects, the device 103 can be a laptop computer with wireless network capabilities and an image capture device. The device 103 can interface with the server 105 via a network, such as a cloud. The device 103 can have an offender app 104 (sometimes referred to as an "app" herein) installed which can communicate with the Offender 101 via the offender interface 102 and communicate with the server 105 via a network connection. The server 105 interfaces with law enforcement 111 via link officer app 106 to a device 108 which has a dashboard 110 for two-way communication.

The server 105 can be in communication with one or more third-party tools 112. The third-party tools 112 can be located in the cloud, on another server, or any other device that can be in communication with the server 112. Communication between the server 105 and the third-party tools 112 is over a secure connection. The third-party tools can be any tool useful for the online monitoring and verification methodology described herein. For example, the third-party tools 112 can be one or more facial recognition algorithms. For example, the third-party tools 112 can be a criminal database maintained by a governmental agency. Other examples of third-party tools 112 are discussed herein.

Figure 3:
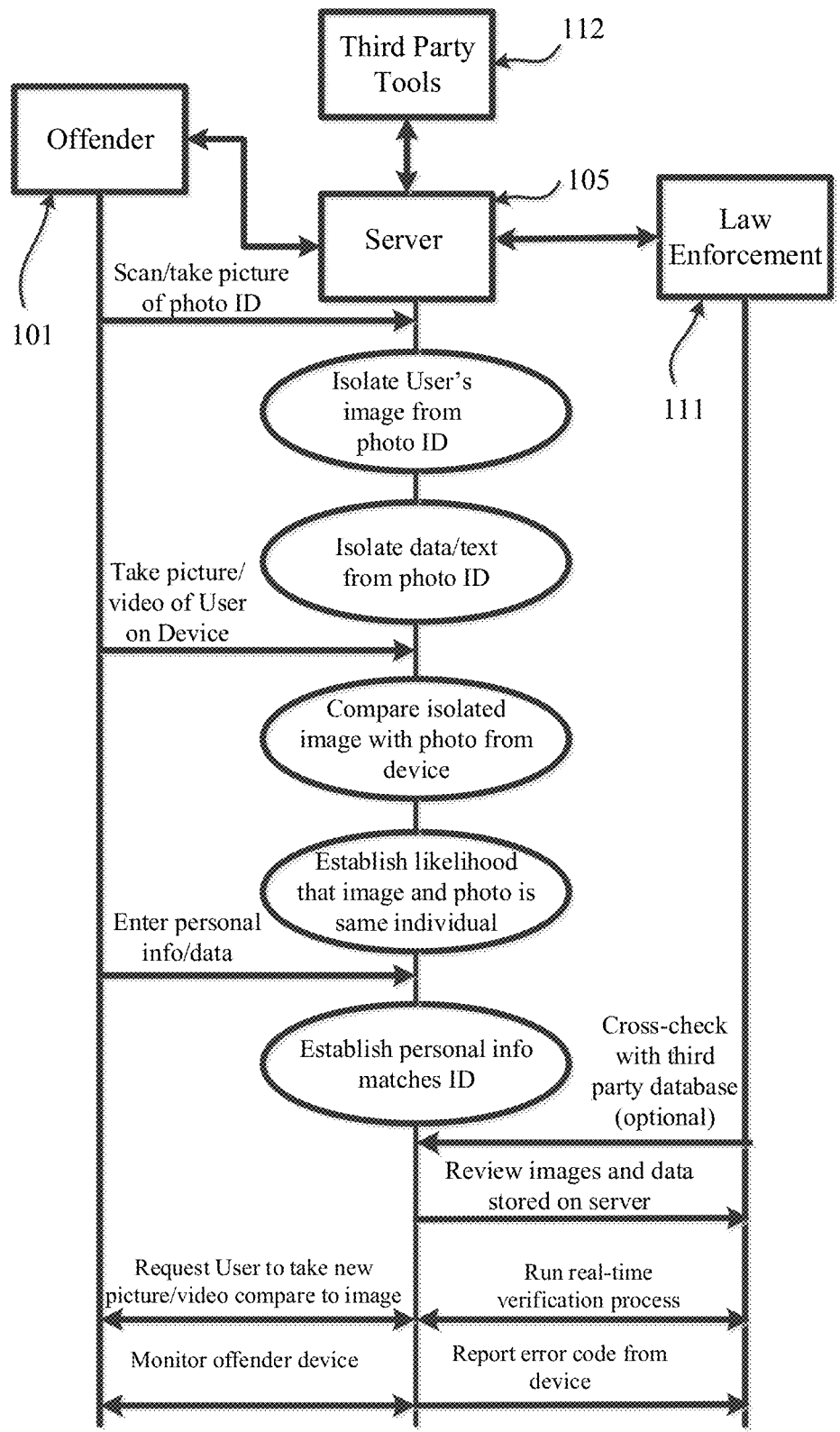
FIG. 3 is a flowchart illustrating an exemplary process flow of verification between the various elements for providing the online verification methods and systems, in accordance with various embodiments.

In FIG. 3, a flowchart illustrates details of an exemplary process flow of verification between the various elements for providing the online verification methods and systems. As illustrated in FIG. 3, offender 101 can use the device 103 to generate an image of an identification card ("ID"), which is stored on the device 103 by verification app 104. A verification engine on the server 105 isolates the offender's image from the ID ("ID photo") and isolates personal data from the text and/or bar code on the ID. In some configurations, the offender 101 enters the information during a meeting with law enforcement 111 and the data is confirmed by law enforcement 111 which can compare the data to the offender's 101 record.

The offender 101 takes one or more pictures or a video of self with the device 103 ("offender photo"). In some configurations, the offender app 104 can be used to confirm that the offender 101 in the picture or video is a live person. In some configurations, the verification engine is on the server 105 can be used to confirm that the offender 101 in the picture or video is a live person.

The offender 101 provides a self-image by using the device 103 to take one or more pictures or video of the offender's face. One or more stills from the video can be compared to confirm that the self-image is that of a live person. In the alternative, two or more pictures compared to confirm that the self-image is that of a live person. These comparisons, using either photos, stills from a video, or a combination of both, can be a "liveness test".

In some embodiments, a "liveness test" can be performed to confirm that the self-image is of a living person. For example, a short video may be taken and the offender 101 is asked to open and close eyes during the video. In an example, the video can be scanned for still images of open eyes and of closed eyes. If both types of images exist, then the self-image passes the "liveness test" and the offender considered a living person. Another example can include a first photo with eyes open and a second photo with eyes close. If both of these photos are sent, then an algorithm can be used to confirm that the Offender's image is that of a living person. For these examples, a smile/no smile could be substituted for the eyes opened/closed. For these examples, a hand on face/no hand on face could be substituted for the eyes opened/closed. As is obvious to one skilled in the art, any number of different positions, gestures, expressions during the self-image photos or video could be used.

In another example, a short video may be taken while moving the camera around the Offender's face, for example moving the camera for ear to ear in a motion that is somewhat perpendicular to the face. In an example, the video can be scanned for different views of the face, which can be used to determine that the Offender face is a 3D object, which passes the test and the offender 101 is a living person (not a photo of a 2D picture).

Another example can include a first photo of the front of the offender's face and a second photo of a side angle of the offender's face. If both of these photos are sent, then an algorithm can be used to confirm that the offender's self-image is that of a living person. In such an example, the angle the photos were taken can be determined by using a gyroscope in the device 103. Of course these and other examples can be combined to send both 3D views of the offender's face and different gestures/expressions on the offender's face to an algorithm to confirm that the offender's self-image is that of a living person.

The verification engine compares the offender photo with the ID photo then establishes the likelihood that the offender photo and the ID photo are images of the same person. The offender 101 enters personal data into the app 104 and the verification engine determines if the entered personal data matches the personal data from the ID. In addition, the validity of the ID is determined by a comparison with an appropriate database. The personal data and images are stored on the server 105. The identification data from the device 103 ("device ID") can be retrieved by the app and stored on the server 105. An offender profile can include the offender photo, the ID photo, the personal information, and the device ID. If the entered personal information and the personal information from the ID matches and the Offender photo and the ID photo are likely the same person, and the ID is valid, then the server 105 sends a token to one or more of the law enforcement 111, which establishes that the offender 101 is verified. The token can be used as or used to establish a verified access key 111, which allows the Offender 101 to interface with the law enforcement 111.

Some optional aspects are also illustrated on FIG. 3. In an option, the law enforcement 111 can request and receive additional information from offender 101, which is used to determine if the offender 101 can be verified. In an option, the server 105 can cross-check the offender 101 against a third-party database, such as, for example, a sexual predator database, criminal history database, credit history, or the like.

In still another option, the law enforcement 111 can require real-time verification from the offender 101. The law enforcement 111 can send a request to the offender 101 to provide a new offender photo within a certain time window. The offender 101 takes a new offender photo, as described herein, which sent to the server 105 and determined if the new offender photo is the same person, who was originally verified. If the new offender photo confirms that the offender 101 is the same person, who was originally verified, then server sends a pass message to law enforcement 111. If the new offender photo is determined not to be the same person, then a fail message is sent to law enforcement 111, which can then initiate action such as filing a warrant or using a second form of communication to contact the offender 101. If the amount of time in which the offender 101 must respond has expired, then a fail message is sent to law enforcement 111, which can then initiate action such as filing a warrant or using a second form of communication to contact the offender 101.

Figure 4:
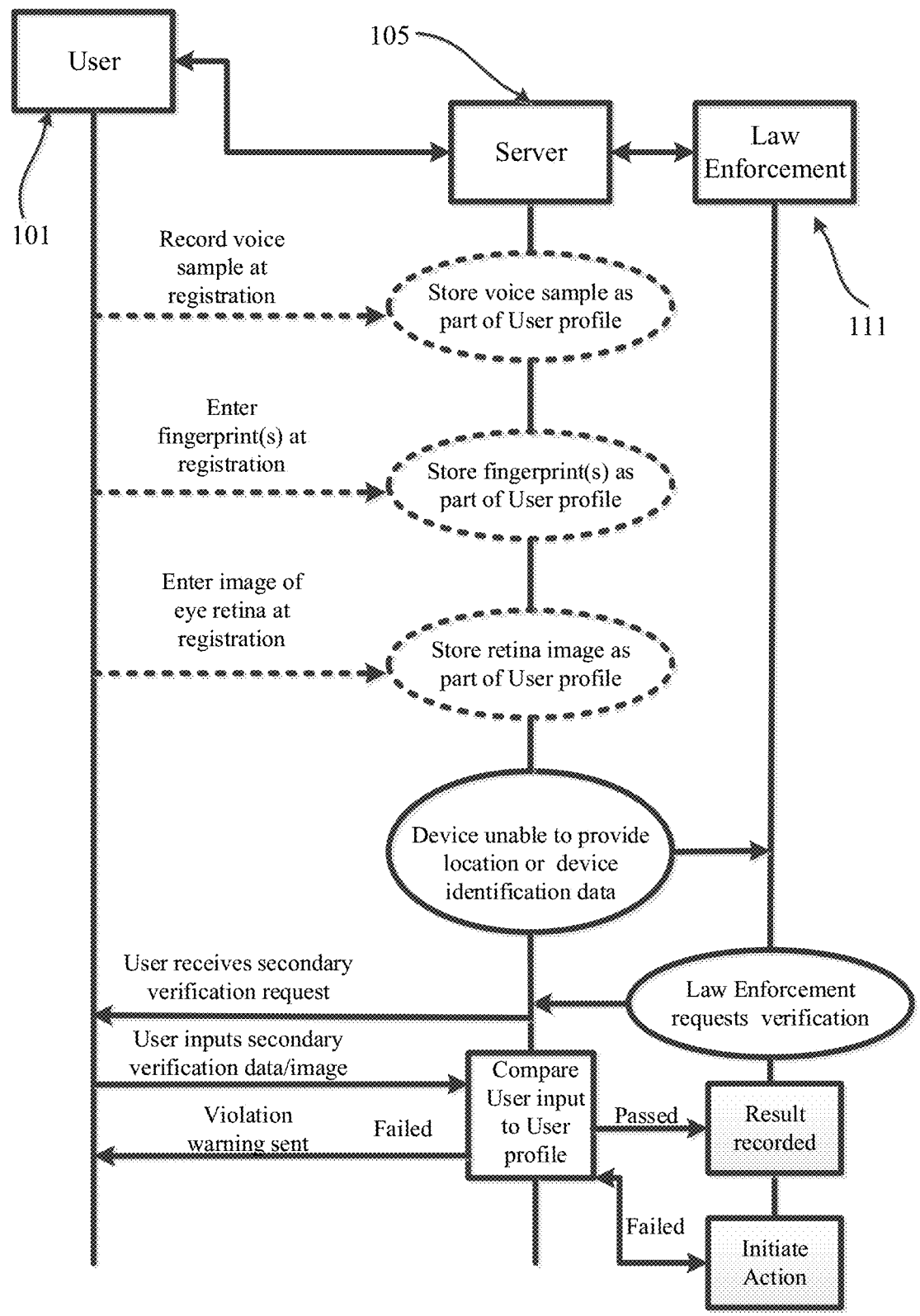
FIG. 4 is a flowchart illustrating an exemplary process flow of secondary verification between the various elements for providing the online verification methods in accordance with various embodiments.

In FIG. 4, a flowchart illustrates details of an exemplary process flow of secondary verification between the various elements for providing the online verification methods. For example, the offender app 104 can be configured to receive and store an initial secondary identifier on the server 105 after the token is created. The law enforcement 111 can request offender 101 for real-time verification, which requires the offender 101 to input a secondary identifier, which is sent to the server 105. The server 105 compares the secondary identifier to the initial secondary identifier and determines if the secondary identifier and the initial secondary identifier are substantially the same. If the secondary identifier confirms that the offender 101 is the same person, who was originally verified, then server sends a pass message to law enforcement 111 If the secondary identifier is determined not to be the same person, then a fail message is sent to law enforcement 111, which can then initiate action such as filing a warrant or using a second form of communication to contact the offender 101. If the amount of time in which the offender 101 must respond has expired, then a fail message is sent to law enforcement 111, which can then initiate action such as filing a warrant or using a second form of communication to contact the offender 101.

Examples of the secondary identifier include, but are not limited to: a voice pattern generated by the offender 101 and captured by a microphone on the device 103; an image of a retina of an offender's eye captured by the device 103; at least one fingerprint of the offender 101 captured by the device 103; a palm scan of the offender 101 captured by the device 103; a photo of the offender captured by the device; a RFID tag tethered to the device 103; and a password. The secondary identifier can be added to the offender profile. Any device can be tethered to device 103 and provides information that can be useful for the monitoring and verification methodology can be used as a secondary identifier. In addition, a blood test and/or breath test may be request during a secondary verification, which can be used to determine if the offender is following the restrictions of their release agreement with the court.

As illustrated in FIG. 4, the offender 101 can enter at least one secondary identifier, which can be any of or all of a voice sample, an image of fingerprint(s), and an image of eye retina, into the device 103. The verification 104 sends the secondary identifier(s) to offender Profile, which is stored on the server 105. When the law enforcement 111 sends a request to the offender 101 for secondary verification, the Offender 101 is required to enter the required secondary identifier, such as, the voice sample, the image of fingerprint(s), and/or the image of eye retina, into the device 103, within a limited time window. For example, within 1 minute of the receipt of the request. If the required secondary identifier is not entered within the limited time window, access to the law enforcement 111 is denied.

The required secondary identifier, as entered by the Offender 101, is sent to the server 105 to be compared to the secondary identifier, which is stored as part of the offender profile. If the Offender input matches the secondary identifier in the offender profile, a token is granted or renewed. However, the law enforcement 111 can limit access within certain geographical boundaries. If the device 103 is outside of the boundaries, then access is denied. However, if the device 103 is outside of the boundaries the law enforcement 111 may require real-time verification to determine if the verified Offender 101 is attempting to access law enforcement 111. In some configurations, the law enforcement 111 can deny access if the device 103 is unable to provide a location or provide device ID.

In some embodiments, the offender 101 downloads the offender app 104 onto the device 103. The offender app 104 can require the offender 101 to enter an offender name and a password to begin the process to establish an account. The offender app 104 is configured to collect all images and data through the device 103. For example, the offender app 104 can control the camera of the device 103 to collect images. For example, the offender app 104 can provide the offender 101 pages with areas to fill in required information/data. The offender app 104 can be a web based application, which is connected to verification engine residing on a server 105 in a cloud that is in communication with the web.

The device 103 is configured to collect all images and data through the verification app 104. The offender 101 enters an email address and a password in verification app 104. If the data fields are confirmed, the offender 101 is then required to take a self-picture/video ("offender photo") with the device 103. If the offender 101 has elected to enter a self-video, still images from the video are isolated. The system can use a "liveness test" to confirm the offender photo is of a live person, who is the offender 101. Methods to confirm that an entered image is of a real and/or a live individual are described herein. Any such tests, methods, comparisons, and/or algorithms can be used here. The ID photo and offender photo are compared, using for example a biometric routine, and the data is used to calculate the statistical likelihood that the ID photo and the offender photo are the same person. If the statistical likelihood is above (greater than) a defined threshold, then there is a Match. For example, the defined threshold can be at least 85% likelihood. In some applications, the defined threshold may be required to be greater than 95%. If the statistical likelihood is below (less than) a defined threshold, then there is a Fail and the Offender 101 is directed back to the page that generates a digital image of ID.

If there is a Match, the GPS location of the ID Card photo and the GPS location of offender photo are compared. If the two GPS locations are substantially the same, then there is a second Match. If the two GPS locations are different, then there is a Fail and the offender 101 is directed back to the page that generates a digital image of ID.

After the second Match, the offender 101 is requested to enter a set of required personal information/data. In the example of FIG. 4, the set of required personal information/data include entering: the last four digits of ID, an email address, the offender name and password, and the phone number of the device 103. However, the set of required personal information/data can be any set of such information/data as provided by any one of the law enforcement 111. The offender app 104 collects the device ID and GPS location.

An application of one or more of the embodiments can include methods and systems for providing online monitoring of released criminals. A law enforcement 111 can connect the verification system through a secure API, which provides law enforcement 111 with the means to deliver verification technology to a supervised offender's 101 device 103. For example, the smartphone can be replaced by a tablet, or any device that has at least a camera, a GPS locator, a network interface, and an offender interface.

By combining a verification app 104 on the device 103 with an enterprise API, the verification systems, as well as, methods thereof, will allow the law enforcement 111 to verify the identity and location of any supervised offender 101, at any time, in any place. The verification system confirms the identity of the offender 101 each time the verification app is activated by a law enforcement 111, such as, for example, a parole officer. The verification system identifies the physical location of the individual offender 101 the moment the app is activated. Using this verification system, the identity of the offender 101 cannot be faked, because it is uniquely tied to both the individual offender 101 and the offender's device 103, as described herein.

The law enforcement 111 can create an offender profile by submitting offender record, including picture (which is at least similar to offender ID, described herein), through the verification API. The offender 103 loads the verification app onto his/her device 103 and is instructed to take a self-picture (or video). In some applications, the offender 101 is instructed to make a voice recording on the device 103. The verification engine matches the self-photo with the offender file photo, and the offender's device 103 becomes their online proof of identity and location, at any time and in any place.

The verification system can utilize the offender file from the law enforcement 111 to obtain the photograph of the offender's face, which is uploaded to the verification system engine. An enforcement app can be loaded onto the offender's smartphone, and can be configured to instruct the offender 101 to allow the app to take a picture of his/her face. When completed, the picture is compared to the picture in the engine using facial recognition technology, and if determined to be a Match, the app will signify that the process was successful. The offender's ID will then be attached to the unique identifier in the device 103 used, so that the offender 101 can carry their virtual ID with them wherever they go.

Supervised offenders 101 can be monitored without physical visits. Offenders 101 are monitored via the verification API from the officer's desk. On-the-spot offender checks can be activated at the officer's discretion, or on a random basis through the system. When activated by the law enforcement 111, the offender's verification app signals that a check is being made. In at least one example, this signal can be equivalent or at least similar to a signal that activates the real-time verification procedures described herein. The physical location of the offender 101 is captured, and the offender 103 is then instructed to allow the app to take a picture (or a video) of his/her face (such as an offender photo described herein). The verification engine then determines if the picture matches the photo in the offender file. Notice will be returned to the law enforcement 111, signifying the result of the facial recognition, and the exact geo-location of the offender 101 at that moment in time. Each time the offender 101 goes through this process, the result will be saved for future reference and use by the law enforcement 111. In some aspects, the outcome of the Match to photo (such as, match, or no match or 95% match, etc.) is provided to the law enforcement 111 along with the physical location of the offender 101. In some aspects of this application, the picture taken by the offender 101 is provided to the law enforcement 111. The photo from the offender file can also be sent along with such a picture for comparison by law enforcement 111. All information gathered from offenders 101, including pictures and locations, is saved in the system for retrieval at any time. This information can be used as evidence in probation/parole violation proceedings.

By using this verification system and/or methods thereof, the offenders 101 can be supervised with fewer personal visits, which will save time and will lower expenses. For sex offenders 101 and other long-term supervised offenders 101, an up-to-date photo record is created with each new check, ensuring that law enforcement 111 has a current likeness of each offender 101 at all times. Photos of offenders 101 can be viewed over time to see if any indications of illegal activities can be discerned. Major short-term weight loss, for example, might be an indication of illicit drug use. Cuts and/or bruises, for example, might be an indication the offender 101 was in a fight or involved in an assault, which might be a violation of the courts conditions of release.

The verification system has the ability to reliably track offender locations, such as, the proximity to specific places and people, for unprecedented visibility into an offender's activities and compliance with court conditions. In addition, the verification system can track whether or not an offender 101 went to off-limits locations like liquor stores and schools, or visited off-limits individuals like former victims and gang members.

In some embodiments, the system utilizes the offender's 101 file from the law enforcement 111 to obtain the photograph (offender ID) of the offender's 101 face, which will be uploaded to the verification system engine on the server 105. The offender app 104 will be loaded onto the offender's smartphone 103, and will instruct them to allow the app 104 to take a picture of their face. When completed, the picture will be compared to the picture in the engine using facial recognition technology, and if determined to be a match, the app will signify that the process was successful. The offender's ID will then be attached to the unique identifier in the smartphone 103 used, so that the offender 101 can carry their virtual ID with them wherever they go.

The law enforcement 111 with the verification API, which will allow them to alert any enrolled offender 101 at any time through the offender app 104. Upon receiving an alert, the offender 101 will be asked to again allow the app 104 to photograph their face. The new photo will be compared to the file in the verification engine, and a notice will be returned to the law enforcement 111, signifying the result of the facial recognition, and the exact geo-location of the offender 101 at that moment in time. Each time the offender 101 goes through this process, the result will be saved for future reference and use by the law enforcement 111.

In some embodiments, the system offers budget-strapped states and counties a less expensive alternative to traditional supervision techniques. Not only does the system significantly reduce the time officers spend following up on offenders 101, such as, probationers and parolees, it's far less costly than other methods. The system can lead to positive, evidenced-based outcomes for decreased recidivism, alleviating the strain on over-crowded jails and prisons. Innovative biometric identity and location verification technology is bundled into a smartphone app 104 tied to a secure, enterprise application program interface (API) 117. Using it is as simple as sending and receiving a text. The system lets supervising officers verify offenders' identity with biometric accuracy, while confirming their exact location through the cellular network.

In some embodiments, the probation or parole officer (law enforcement 111) creates an offender profile through the verification API 116. Then, the offender 101 downloads the offender app 104 to his smartphone 103 and takes a selfie with the phone's camera, establishing biometrics. Verification engine creates a verification file, and the offender's smartphone 103 becomes digital proof of identity and location, wherever the offender 101 goes. Law enforcement 111 can pre-schedule the verification requests to confirm that offenders 101 are attending counseling or treatment, or that they are abiding by curfews. A Verified Message Module allows law enforcement 111 to send "verified" messages to offenders 101, providing court-admissible proof that the offender 101 received the message and eliminating the "I never got the message" excuse. Evidence provided by the powerful reports and mapping engine can be used in violation hearings, or to confirm that an offender 101 is complying with release terms. With the system, officers (law enforcement 111) conducting field activities can instantly pinpoint the location of an offender 101 and cut down the number of home or work visits they make—saving time, money, and precious resources.

Law enforcement 111 can supervise an offender 101 under house arrest or alternative confinement by using the system to conduct regular or randomize checks, ensuring that the offender 101 remains at his residence. The intervals and frequency of checks can be set with precision, using the officer dashboard. the verification system also eliminates the exhaustive effort required to monitor transient offenders 101, easily identifying those who claim to be homeless, but actually have residences.

Officers (law enforcement 111) in the field can use a Field Officer App to monitor and supervise effectively while conducting operations in the community. Officers (law enforcement 111) can utilize all the features of system from their own smartphones, instantly sending verification requests 116 or reviewing reports, locations, and pictures of offenders 111.

The system can also be used on high risk, gang, or registered sex offender caseloads as an affordable alternative or an add-on tool to traditional GPS supervision. For registered sex offenders 101 and other long-term supervised offenders 101, each new verification creates an up-to-date photo record, ensuring that law enforcement 111 always has the most current likeness of an offender 101.

In a time of wide-spread budget slashing, banked caseloads, and overextended probation and parole officers, the need for efficiency has never been greater. Departments need affordable, innovative technology to work smarter. In an ideal world, offenders 101 successfully complete probation or parole and return to their communities as productive citizens. The system supports these outcomes while keeping the community safe and at the same time allowing supervision officers to spend more time with serious offenders.

Figure 5:
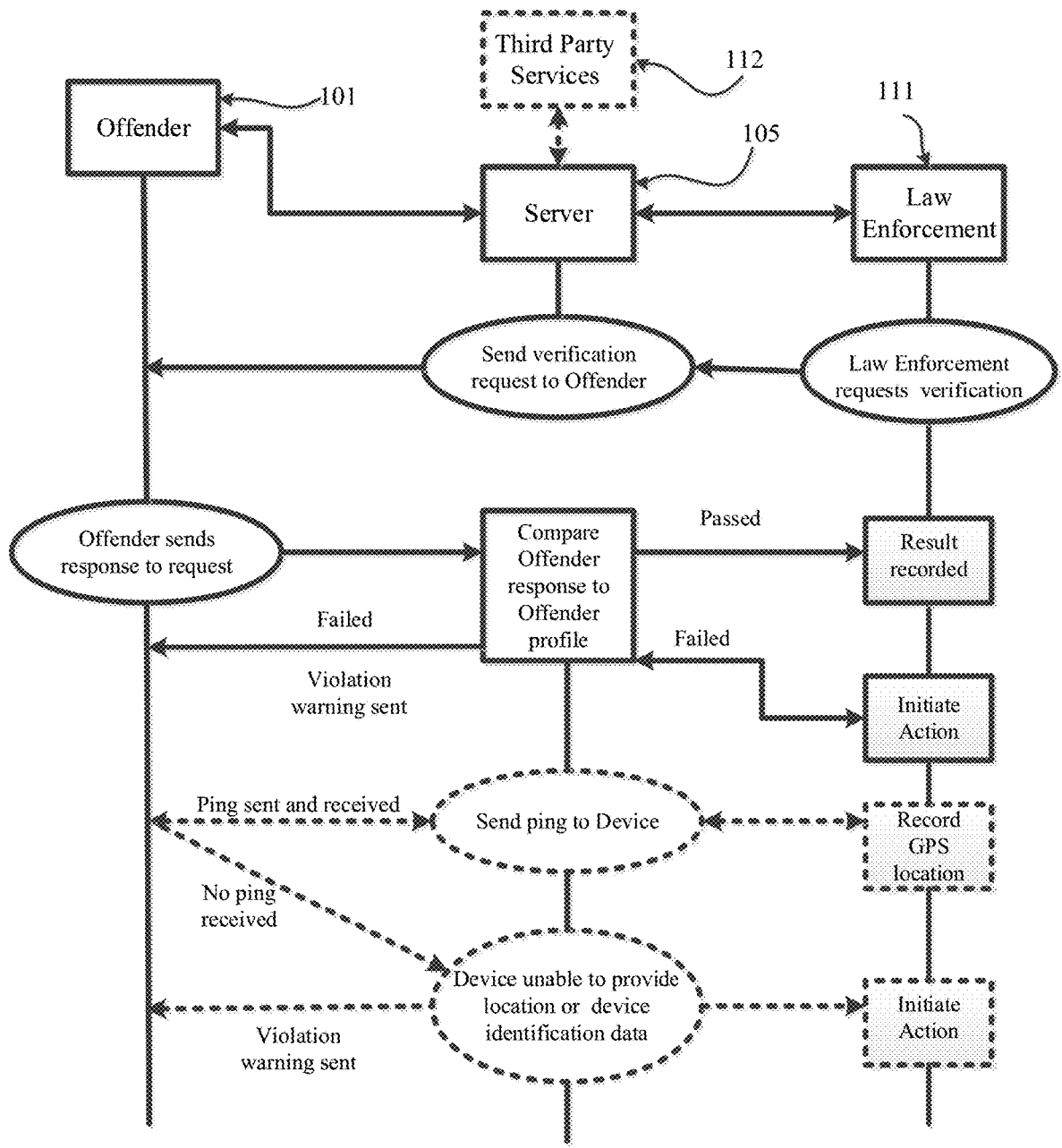
FIG. 5 is a flowchart illustrating an exemplary process flow of a verification process, in accordance with various embodiments.

As illustrated in FIG. 5, a flowchart illustrating an exemplary process flow of a verification process. As discussed herein, law enforcement 111 can send a verification request to the offender 101. The offender 101 must respond within a specified amount of time using the device 103. The offender 101 responds to the verification request and the image sent with the response is compared to the offender profile. If the comparison is a Match, then the verification passed. A message can be sent to the device 103 to confirm the verification. If the comparison is a Fail, then law enforcement 111 is alerted and can initiate action that is appropriate for the verification failure. A violation warning can be sent to the device 103 to inform offender 101 of the failure.

In some aspects, a ping can be set to the device 103. If the ping is returned, the GPS coordinates of the location of the device 103 can be retrieved from the app 104 running in the background. These GPS coordinates can be recorded. If no ping is received, then the device 103 cannot provide any GPS coordinates. The device 103 can be turned off, broken, or in an area without service. A violation warning can be sent to the offender 101. If no ping is received law enforcement 111 is alerted and can initiate action that is appropriate for the verification failure.

Figure 6:
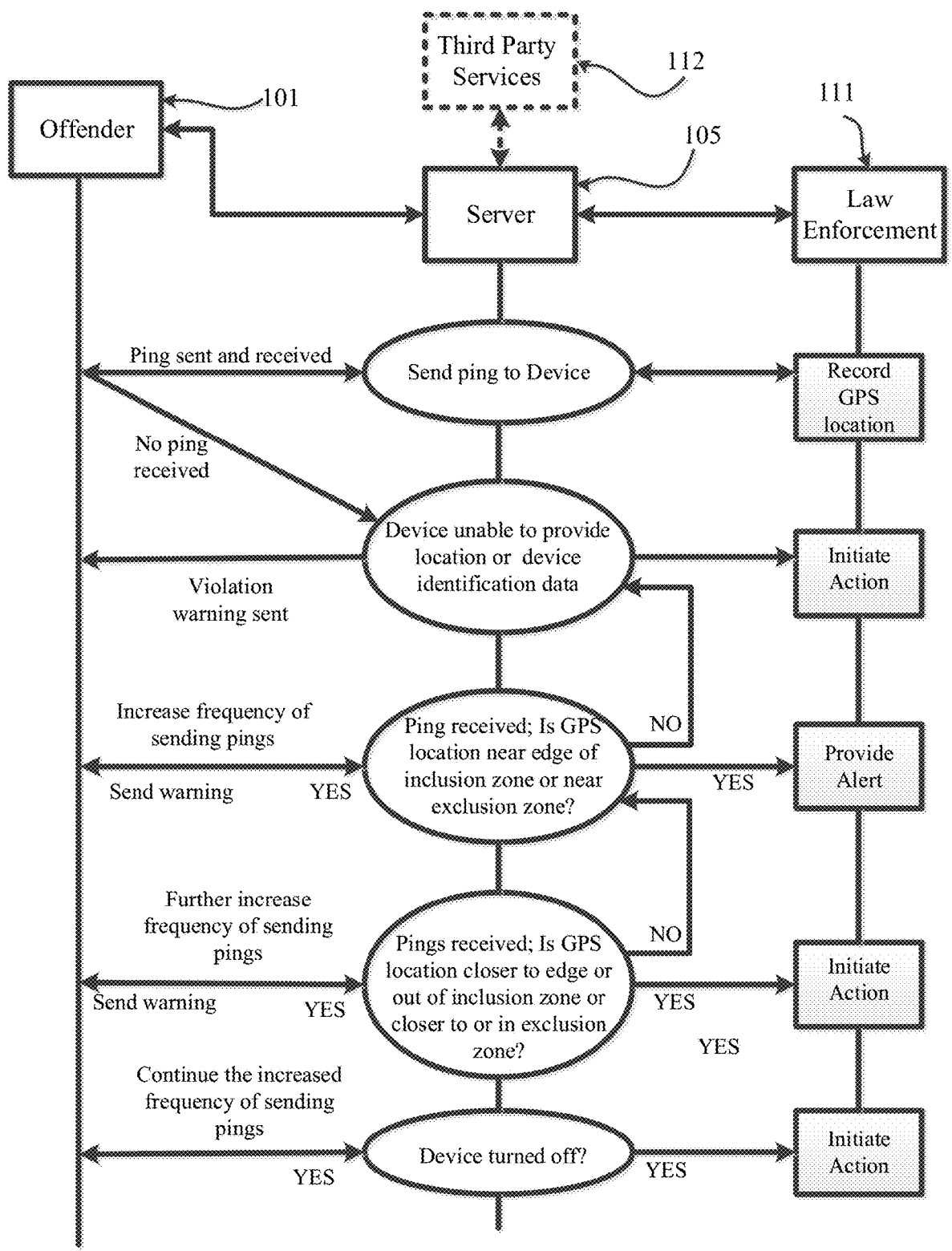
FIG. 6 is a flowchart illustrating an exemplary process flow of a location and response process, in accordance with various embodiments.

Turning to FIG. 6, a flowchart illustrates an exemplary process flow of a location and response process. As discussed, a ping can be set to the device 103. If the ping is returned, the GPS coordinates of the location of the device 103 can be retrieved from the app 104 running in the background. These GPS coordinates can be recorded. If no ping is received, then the device 103 cannot provide any GPS coordinates. The device 103 can be turned off, broken, or in an area without service. A violation warning can be sent to the offender 101. If no ping is received law enforcement 111 is alerted and can initiate action that is appropriate for the verification failure.

A GPS pursuit system can be employed by the verification system. An inclusion zone is an area that the offender 101 is restricted to. For example, if an offender is under house arrest, then the inclusion zone is the offender's residence. The court may allow the offender 101 to go to work, which also be in the inclusion zone. The GPS tracking of the verification system using the device 103 can record if the offender is in the inclusion zone. If the recorded GPS coordinates indicate that the offender 101 is leaving an inclusion zone, the frequency of the pings automatically increases. For example, instead of a normal frequency of a ping every 5 minutes, the frequency may be increased to a ping every minute as the edge of the inclusion zone is nearby. If the offender is at the edge of the inclusion zone or outside of the inclusion zone, the frequency rate of the pings can be increased to a ping every 30 seconds or faster. The increase in rate can be inversely protional to the distance that the offender is to the edge of the inclusion zone. For example, as the offender 101 nears the edge of the inclusion zone, the frequency of the pings increases with each step the offender 101 nears the edge of the inclusion zone. Law enforcement 111 can be alerted and initiate appropriate action when an offender 101 is leaving the inclusion zone.

An exclusion zone is the opposite of an inclusion zone. An exclusion zone is an area, which the offender 101 is not allowed. For example, the exclusion zone can be a residence of a victim. The GPS pursuit can be used similarly to that discussed above except the frequency of pings increases as the offender nears the exclusion zone. If the offender is in the exclusion zone, the frequency rate is increase to its fastest rate and law enforcement is notified. In some aspects, the frequency rate is locked on the fastest rate after the offender 101 leaves the exclusion zone, which allows law enforcement 111 to track down the offender 101, if necessary. The GPS pursuit can provide evidence of the offender 101 in the exclusion zone and the escape route of the offender 101, if a crime has been committed in the exclusion zone.

Figure 7:
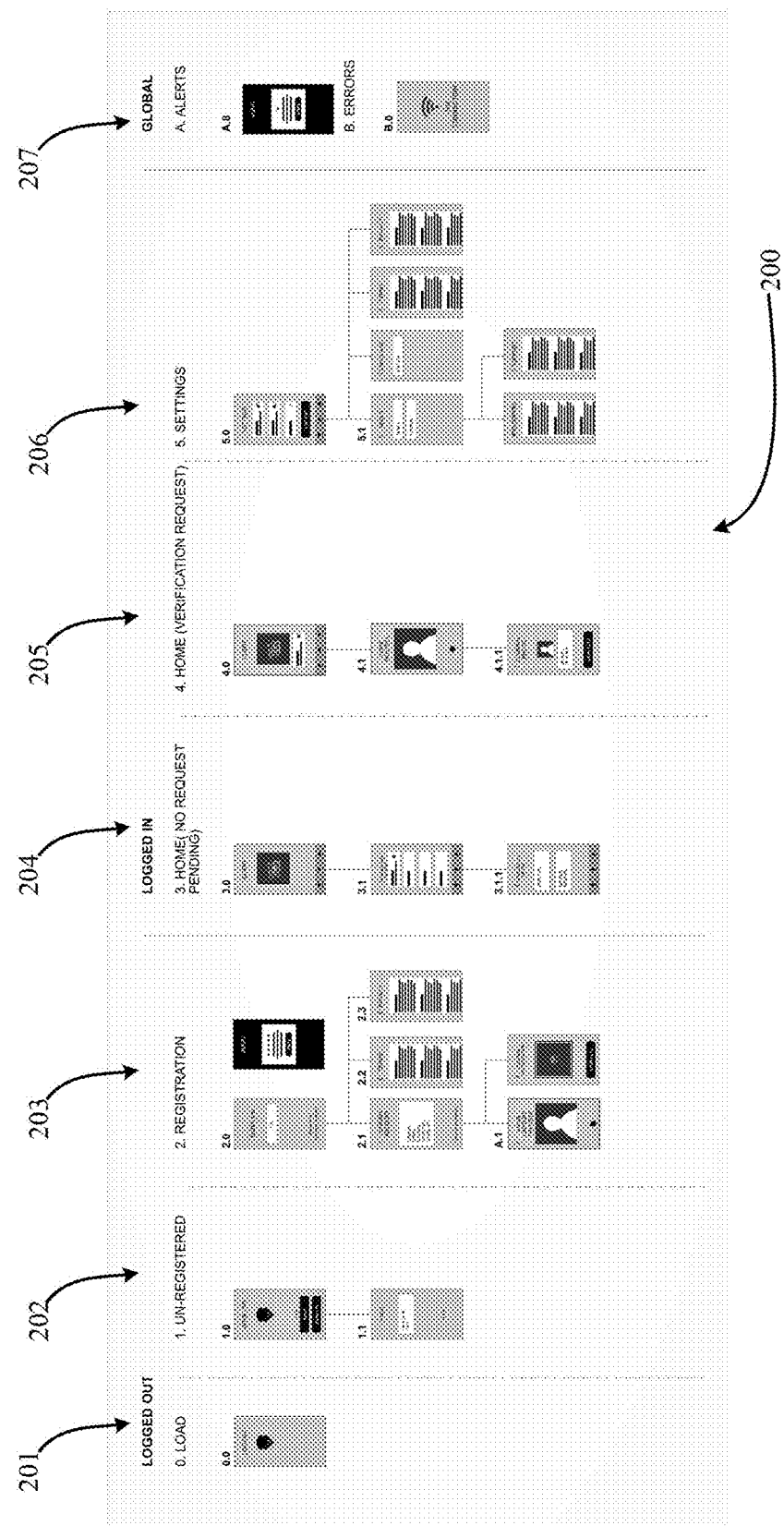
FIG. 7 is a schema illustrating various sections of the online verification system, in accordance with various embodiments.

Now turning to FIG. 7, a schema 200 illustrates various sections of the online verification system. Load 201 is a device that does not have the verification app 104 loaded on the device 103. Un-registered 202 is a device that has the verification app 104 installed but the offender 101 has not registered. Registration 203 is the screens used to allow the offender 101 to be enrolled in the verification system. The sections of Load 201, un-registered 202, and registration 203 operate with the device 103 logged out of the verification system. Home no pending 204 is the verification app 104 without any verification requests pending. Home pending 205 is the device 103 has received a verification request. Home pending 205 goes through the steps for verification, as discussed herein. Settings 206 include various setting for the verification app 104 and/or setting on the device 103 as controlled by the verification system. Global 207 can include updates to the verification app and error codes.

Figure 8:
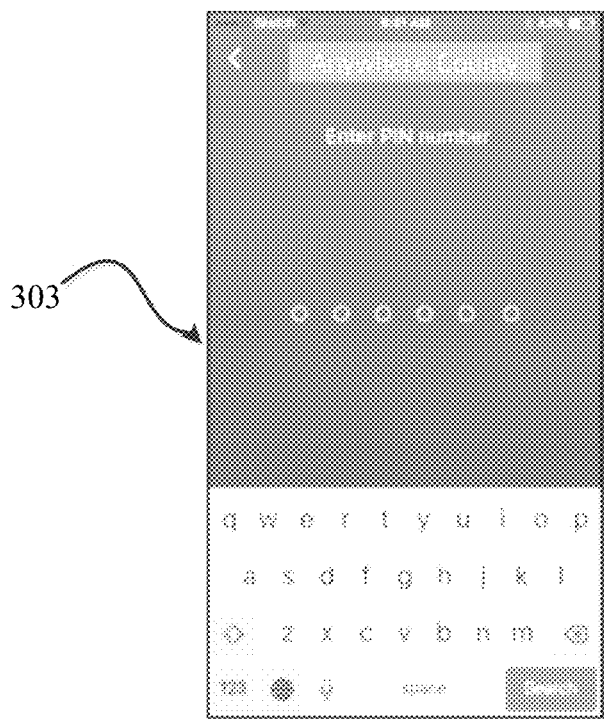
FIG. 8 is a screen shot of a device operating the online verification system, in accordance with various embodiments.
Figure 9:
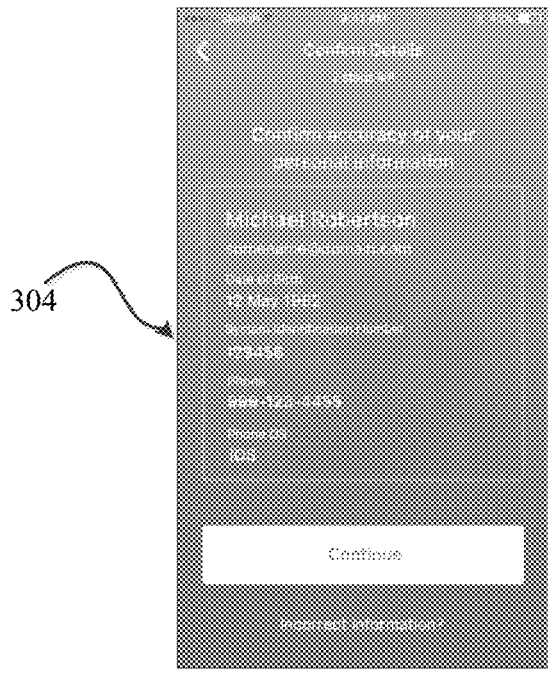
FIG. 9 is a second screen shot of a device operating the online verification system, in accordance with various embodiments.
Figure 10:
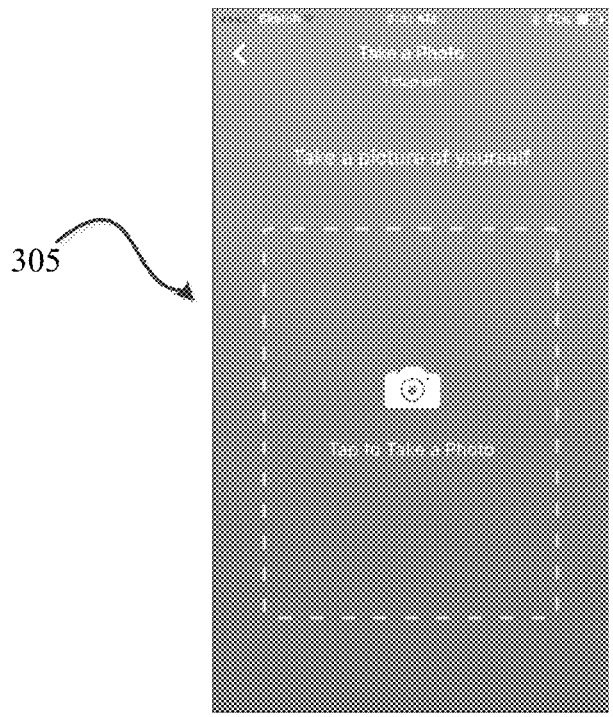
FIG. 10 is a third screen shot of a device operating the online verification system, in accordance with various embodiments.
Figure 11:
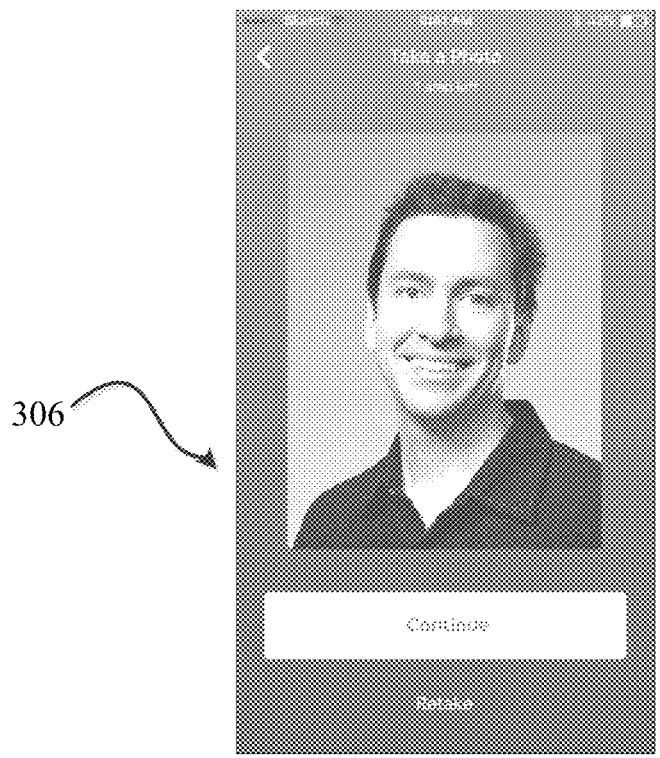
FIG. 11 is a fourth screen shot of a device operating the online verification system, in accordance with various embodiments.
Figure 12:
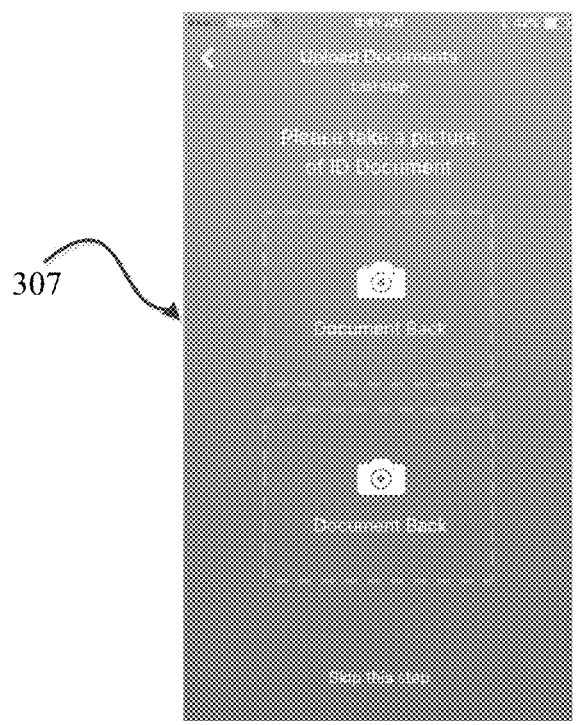
FIG. 12 is a fifth screen shot of a device operating the online verification system, in accordance with various embodiments.
Figure 13:
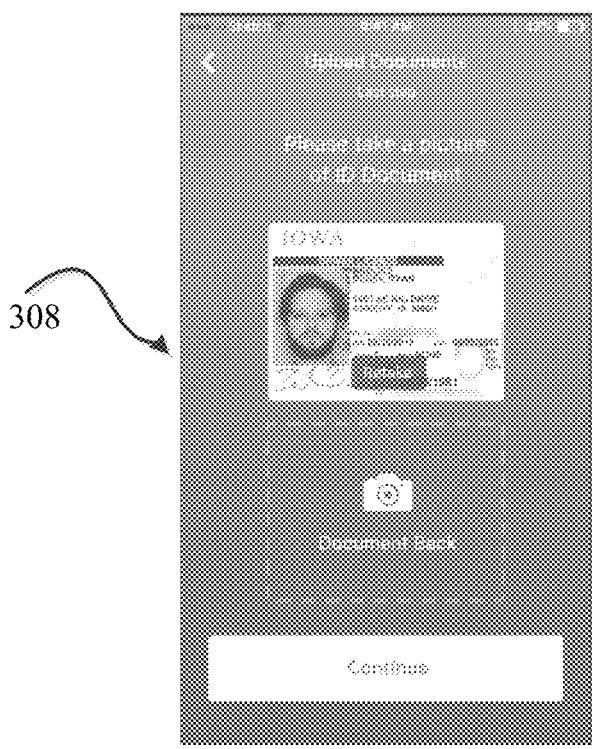
FIG. 13 is a sixth screen shot of a device operating the online verification system, in accordance with various embodiments.
Figure 14:
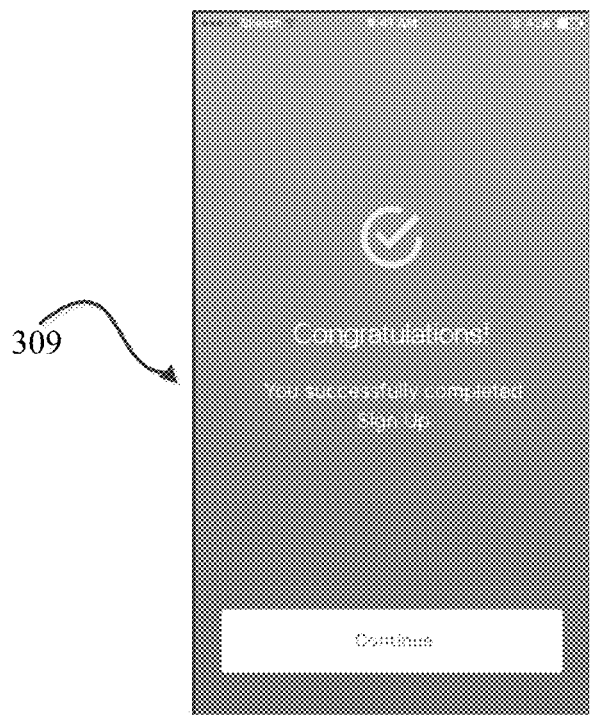
FIG. 14 is a seventh screen shot of a device operating the online verification system, in accordance with various embodiments.

An exemplary method of enrollment and verification is illustrated in a set of screen shots from the device 103, as illustrated in the FIGS. 8-19. The screenshot 303 illustrated in FIG. 8 is a PIN entry, which can come up after the verification app 104 is loaded on the device 103. The PIN is provided by law enforcement 111 confirm the offender 101. The screenshot 304 illustrated in FIG. 9 is a confirmation of personal information and allows for the information to be corrected, which is reviewed by law enforcement 111. The screenshot 305 illustrates the target and trigger for the offender 101 to take a selfie. The screenshot 306 illustrates the image of the offender selfie. The screen shot 307 illustrated in FIG. 12 is the target and trigger for the offender 101 to take pictures of the front and back of the offender ID. The screenshot 308 illustrated in FIG. 13 illustrates an image of the offender ID. The screenshot 309 illustrated in FIG. 14 indicates that the offender 101 successfully enrolled into the verification system if the images of the selfie and the offender ID match. The screenshot illustrated in FIGS. 8-14 can correspond to registration 203 in FIG. 7.

Figure 15:
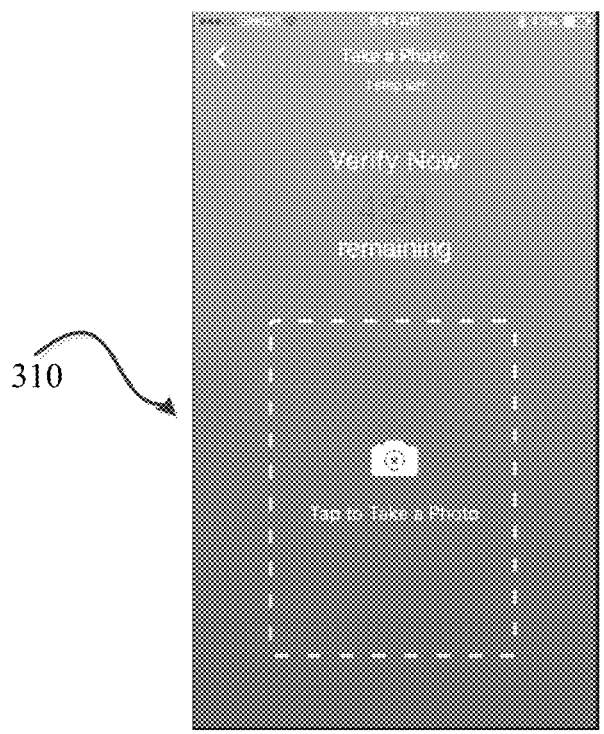
FIG. 15 is an eighth screen shot of a device operating the online verification system, in accordance with various embodiments.
Figure 16:
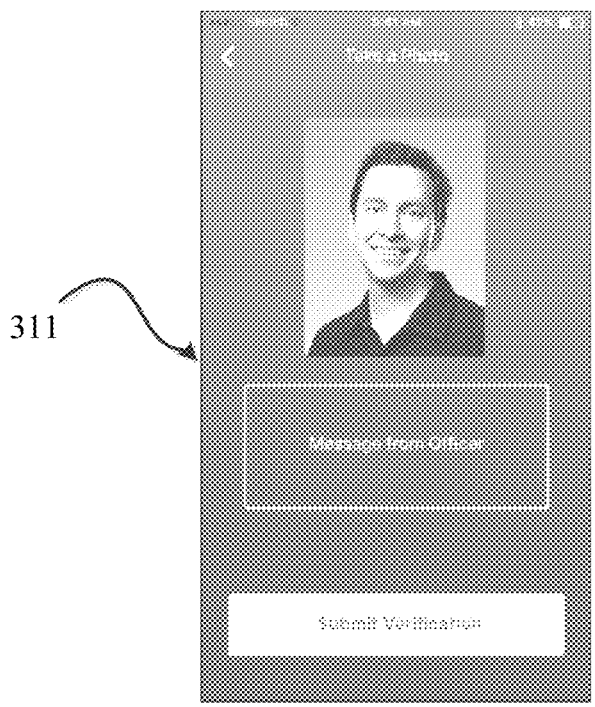
FIG. 16 is a ninth screen shot of a device operating the online verification system, in accordance with various embodiments.
Figure 17:
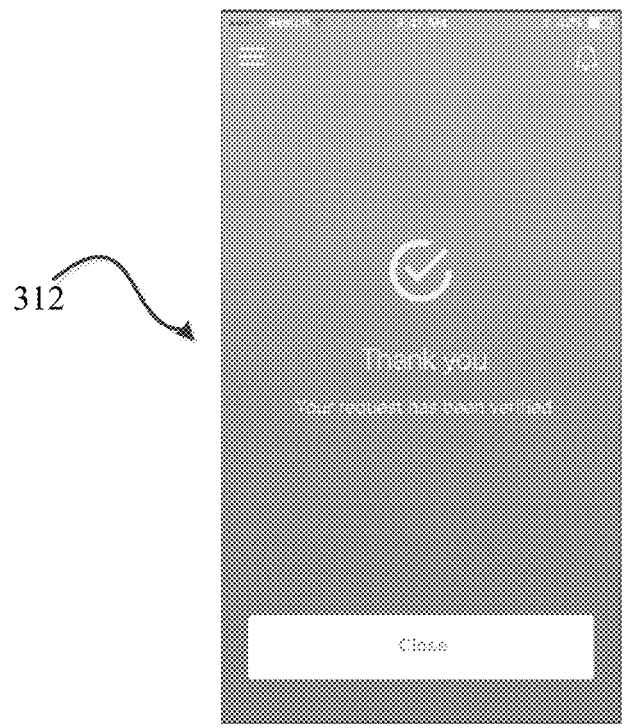
FIG. 17 is a tenth screen shot of a device operating the online verification system, in accordance with various embodiments.

FIGS. 15-17 show screenshots from the verification process. The screenshot 310 illustrates the target and the trigger for the offender 101 to take a real time selfie. A countdown clock is included in the screenshot 310. The screenshot 311 illustrates the image of the real-time selfie of the offender 101, along with the button to submit the verification. Also in the screenshot 311, an optional field for text messages from law enforcement 111 can be provided. The screen shot 312 confirms the verification was successful. The screenshots illustrated in FIGS. 15-17 can correspond to home pending 205 in FIG. 7.

Figure 18:
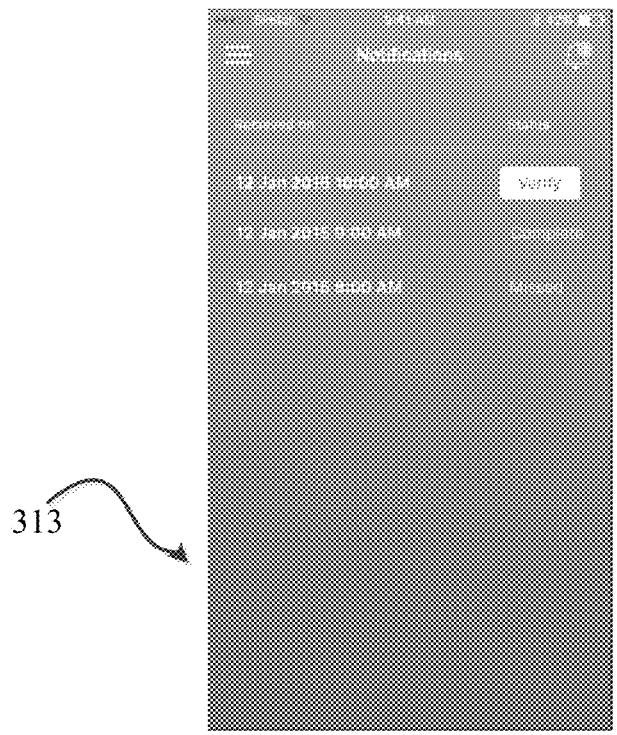
FIG. 18 is an eleventh screen shot of a device operating the online verification system, in accordance with various embodiments.
Figure 19:
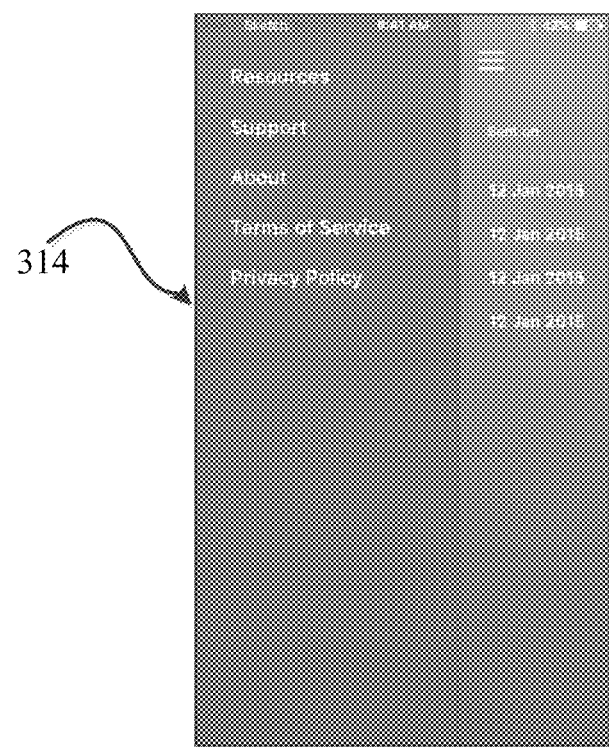
FIG. 19 is a twelfth screen shot of a device operating the online verification system, in accordance with various embodiments.

The screenshot 313 illustrated in FIG. 18 shows a log of verification requests and the outcome of each request. The screenshot 314 illustrated in FIG. 19 illustrates the other features that can be accessed in the verification app 104.

Figure 20:
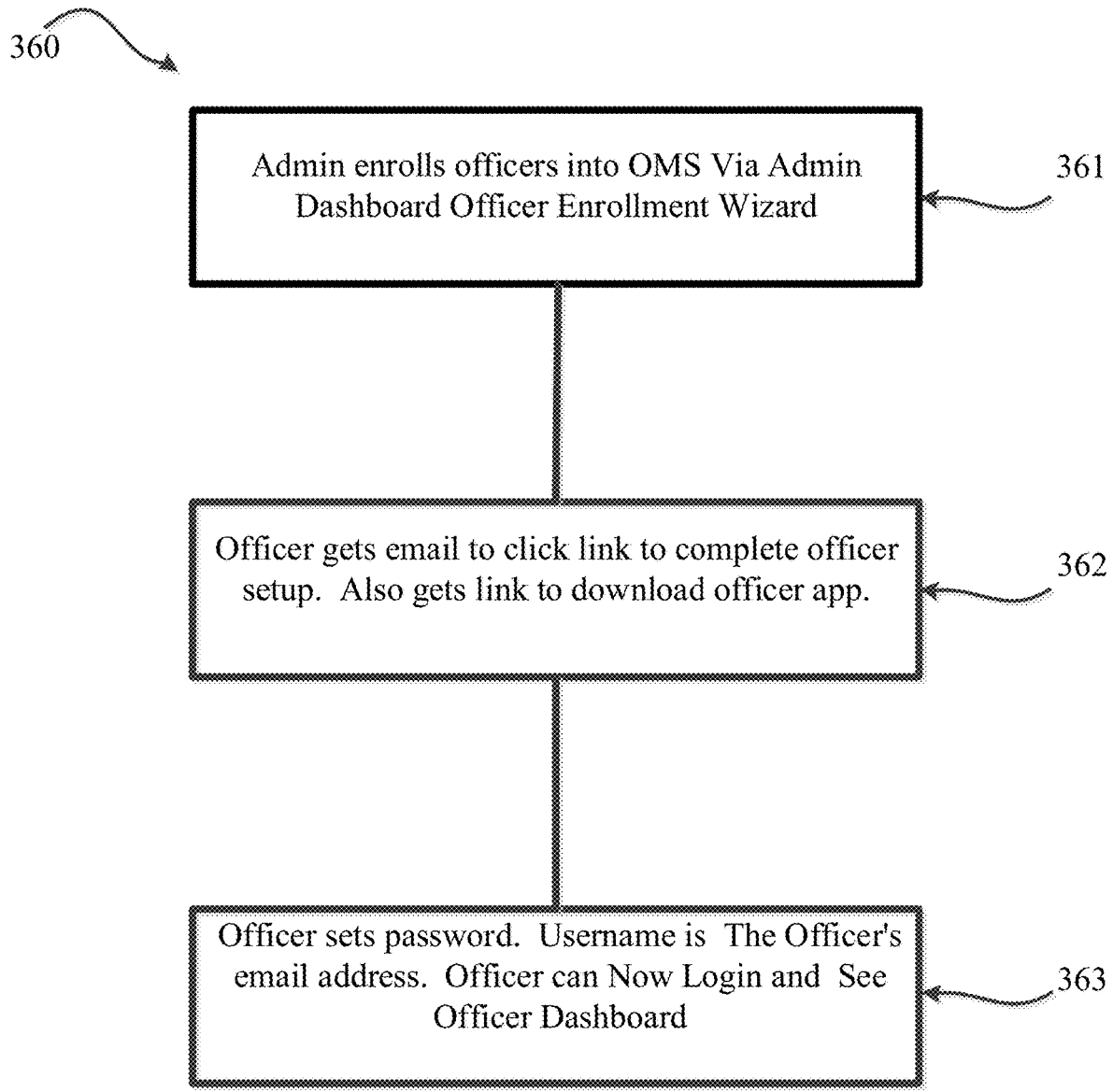
FIG. 20 is a block diagram illustrating a set up process of an exemplary officer dashboard, in accordance with various embodiments.
Figure 21:
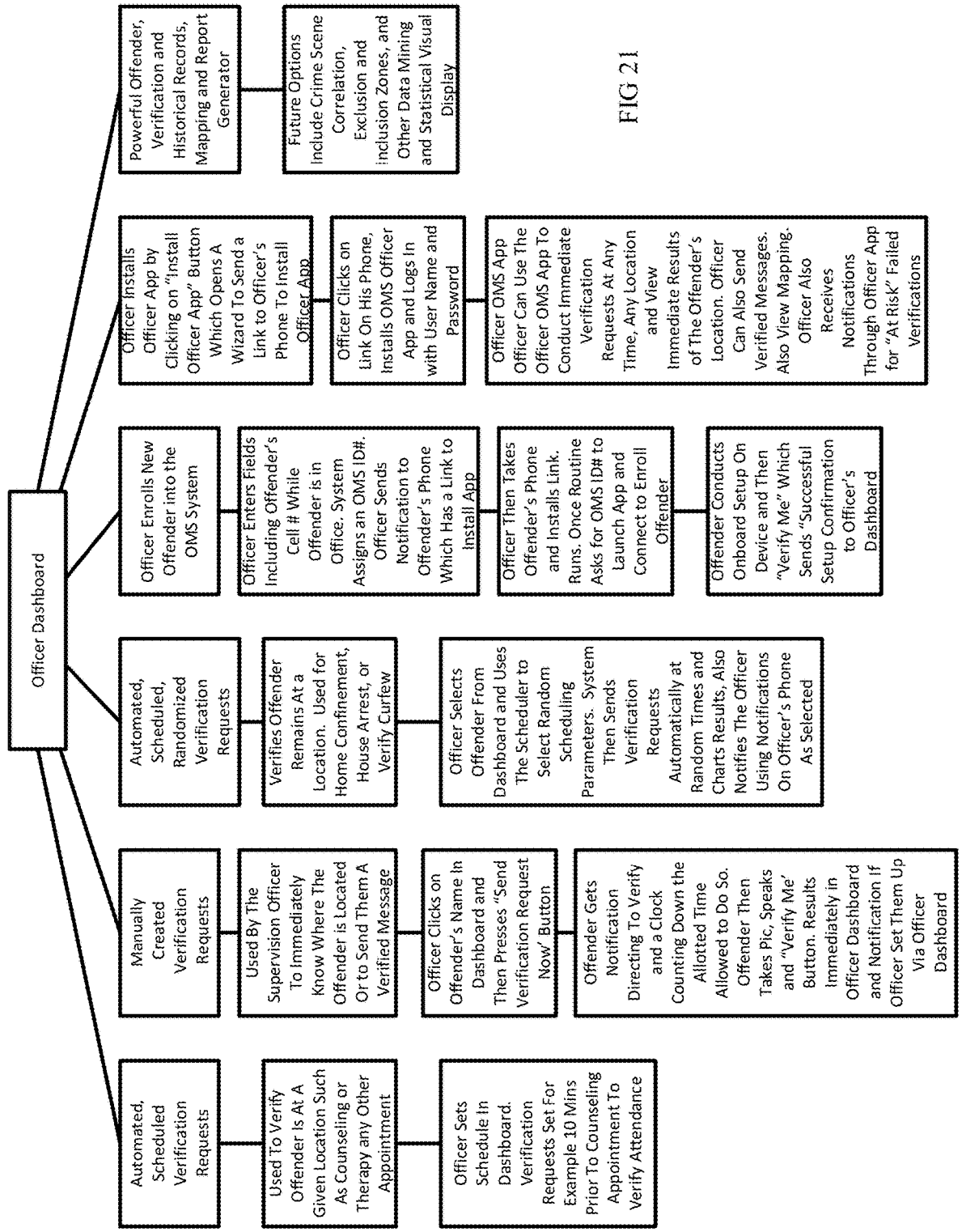
FIG. 21 is a block diagram illustrating the exemplary officer dashboard, in accordance with various embodiments.

An example of a law enforcement dash is illustrated in FIGS. 20 and 21. In some embodiments, The Offender Management Service (OMS) is comprised of four different user interfaces in addition to the backend processes. Defining these environments is critical to seamless deployment and effective product use, especially by new users who are unfamiliar with the OMS environment.

In the course of product development and design one must always consider the audience. Modern law enforcement 111 are not always the most technically advanced personnel. The GUI therefore, must be as simple and self-explanatory as possible. Buttons should be large and screens easily navigable. Simplicity and ease of use are critical. In addition, because so many probation officers and agents have been using GPS tracking products for so many years, they are used to a particular design and the OMS interface should be similar. Lastly, this recommendation includes new features such as the Officer App, messaging, and the use of inclusion/exclusion zones. Such additions will be depicted in highlighted text.

In some configurations, the OMS system should contain four distinct user interfaces. 1) The Admin Dashboard for use by the Probation or Parole supervisor. 2) The Officer Dashboard for use by the Probation officer or Parole Agent. 3) The Offender app, both IOS and Android. 4) The Officer app, both IOS and Android.

The processes are often not visible to the user, but should include: Setup and Onboarding and a dashboard. In an example of the Supervisor dashboard 360: Supervisor adds officers into the OMS system 361 by selecting them from a scrolling list. If no list then prompted for name, email, and Tel# of officers to be provided access. Supervisor deletes officers the same way and can also monitor all officers and verification requests. When selected, clicks on "add" to add officer and send confirmation email. Officers receive email indicating they need to click a link to complete registration and select password etc. Email 362 also includes a link to download the officer app from ITunes/GPlay.

Officer clicks on link, Officer dashboard opens and prompts for password/repeat password. Username is officer's email address. Officer is able to log onto dashboard 363 from any device in a browser (responsive interface) or onto the Officer app with username and password. In Dashboard, officer can add or remove probationers or parolees by scrolling a list from CMS and can search by name, ML# (from CMS), or by unit, or sort list by same. In app, officers can send verification requests, send messages with requests, and enable notifications on their phone for verification request results. In app, officer can also review past verification requests, view results, view map with results. They can filter and sort from this view by offender name, date, successful or failed verification. Notifications on officer app have hot link to app map of location of offender which also details geocode information. Officer Dashboard and app have a single button to "verify offender now". Then gets a prompt to add a message and "Send". Officer Dashboard has a button for "Map" which shows sortable, historical verification attempts graphically on a map. In some examples, the Officer Dashboard has tab or button to "Schedule verification requests". Opens scroll box to select offender(s) for schedule and then allows to select time/date, or recurring. Has a prompt for "add message" and then a box to do so and "send".

In some embodiments, the offender app can be used at Indoctrination or at first office appointment officer has offender sign enrollment documents. While offender is in office, officer opens officer dashboard and highlights offender's OMS entry. Officer is prompted to verify offender's cell phone number and email address and can verify by calling offender's phone. While looking at record on officer dashboard, officer clicks on "Activate offender Phone" (or similar) Offender receives an SMS message with a link to download the app. (Officer should have phone in his/her possession at this point)

The Offender App prompts for "Activation Code" which is being displayed on officer's dashboard after the "Activate Offender phone" is pressed. Activation code is always displayed on officer dashboard as a field for future reference. Prompt for Activation code is a "run once" task. Offender then completes the verification tasks (smile, wink for a liveness test etc.) And "congratulations you have been verified." Displays and first verification request is logged in Officer Dashboard as successful.

A verification request appears on offender's device 103 as a Notification. Pressing the notification will launch the app. The notification says something like: Offender 101—Verify yourself within 5:00 minutes. If possible this clock should countdown on notification. It should display prominently in the offender app. The offender 101 can launch offender app 104 by pressing the notification or pressing the offender app Icon.

In some application, the offender 101 is required to wear a secure continuous remote alcohol monitoring ("SCRAM") monitor, which can detect any alcohol consumption via transdermal measurements throughout the day. If the SCRAM monitor send an alert signaling the detection of alcohol, the verification system can send a signal to instruct the offender to take a picture (or video) of his/her face. In addition, the verification system can send a signal to instruct the offender record a voice sample, which repeats a paragraph provided by the system. In some aspects the voice sample has to be repeated within a predetermined amount of time or it is a failure, which may indicate the offender has been drinking alcohol. The voice sample may be in response to a standard drunk driving test. These signals can be sent by the verification periodically or randomly over a period of time after receiving the alert, which further can confirm the offender has been drinking alcohol. The location (GPS data) collected at the time of each picture can be used to identify bars, liquor stores, club, etc., at which the offender may be drinking alcohol. At least one of the picture, the GPS data, and the voice sample can provide evidence that the offender has been drinking alcohol, which can be used in any probation/parole violation hearing.

In addition, the verification application can verify that the ID Info is valid via a comparison with the appropriate governmental records. For certain applications, the verification application can verify that the ID Info is not on the National Sexual Predator List or similar sexual predator database. The location record, such as, the GPS data can be compared to offender's residence. If the GPS data shows that the offender been at residence over a period of time, law enforcement can send the offender a request of proof of residence. At that point, the offender can provide the proof of residence or update the address of the residence. If neither the proof nor the update is provided by the offender, an alert signaling a possible violation of a court order or terms of probation/parole will be sent to law enforcement. If the residence is updated, then the verification system can send this information to the National Sexual Predator List or similar sexual predator database. Similarly, if the GPS data shows that the offender not been at place of employment over a period of time, law enforcement can send the offender a request of proof of employment. The GPS data can be collected on a continuous basis, or can be collected randomly, or can be collected with picture of offender in response to a request from law enforcement.

During a law enforcement initiated check-in by the offender, the verification engine can scan the offender's name across criminal arrests records and/or review the offender's credit history. Results can be forwarded to law enforcement to determine if any violations of the release conditions have occurred. The verification system can be configured to receive request, an emergency notification, or other communication from the offender. Face to face meetings can be set up using the verification system. In some aspect, the verification system automatically sets up a face to face meeting based on various tests, such as, multiple failures to send a picture in response to a request, or multiple movements outside the boundaries as identified by the GPS data, or time between face to face meetings.

The verification system can be configured to track offender's movements using GPS monitoring. The verification system can be in communication with a GPS ankle monitor, which is constantly monitoring the offender's movements. The verification system can be configured to track offender's movements using the GPS feature on the smartphone.

The system can include an interface between the verification engine and the law enforcement law enforcement. The interface can be configured to send verification parameters from law enforcement law enforcement and to receive results from verification engine. The system can include an interface between the verification token and the law enforcement law enforcement wherein the interface is configured to notify the law enforcement law enforcement that the verification token has been sent to the offender. The token can be sent to the offender to validate the successful verification of picture of offender and location of offender.

Other applications of the methods and systems can include government agencies, for example, parolee surveillance, tracking sexual predators, prevent IRS fraud, prevent Medicare fraud, and many other examples. An application of the methods and systems can include the use in on-line C-to-Commerce sites and/or on-line B-to Business sites.

The methods and systems can provide a source of data collection for each time a token is used or an offender logs in. Other examples of data collection can include the tracking of: when was it used (time/date), device it was used from, device ID it was used from; website/service where it was used; product that it was used for; number of times token was checked/verified by outside offenders; sites on which those verifications took place; products for which those verifications took place; device from which those verifications took place; and demographic information on offenders that verified an ID.

As used herein, the phrase "at least one of A, B, and C" can be construed to mean a logical (A or B or C), using a non-exclusive logical "or," however, can be contrasted to mean (A, B, and C), in addition, can be construed to mean (A and B) or (A and C) or (B and C). As used herein, the phrase "A, B and/or C" should be construed to mean (A, B, and C) or alternatively (A or B or C), using a non-exclusive logical "or."

The present invention has been described above with reference to various exemplary embodiments and examples, which are not intended to be limiting in describing the full scope of systems and methods of this invention. However, those skilled in the art will recognize that equivalent changes, modifications and variations of the embodiments, materials, systems, and methods may be made within the scope of the present invention, with substantially similar results, and are intended to be included within the scope of the present invention, as set forth in the following claims.

The invention claimed is:

1. A system for registering and monitoring a criminal offender over a network, the system comprising:
    an app downloadable to a device comprising a camera, a GPS locator, a network interface, and a user interface, the app comprises:
        a process to initiate an offender to take and capture a picture of an offender's face with the camera;
        a process to capture a first set of GPS coordinates, a first time and a date of the picture of the offender's face;
        a process to initiate the offender to take and capture a picture of an identification card with the camera;
        a process to capture a second set of GPS coordinates, a second time and a date of the picture of the identification card;
        a process to capture identification data of the device;
        a process to send data comprising at least one of the picture of the offender's face, the picture of the identification card, the first set of GPS coordinates, the second set of GPS coordinates, the first time and date of the picture of the offender's face, the second time and date of the picture of the identification card, and the identification data to a location on the network; and
        a process to receive and communicate information;
    an identification engine on a server at the location on the network, the identification engine comprising:
        an input configured to receive the data from the app;
        an image comparison algorithm configured to compare the picture of the offender's face, the picture of the identification card, then determine the likelihood that the offender and a person in the picture of the identification card are substantially the same; and
        a time comparison algorithm configured to determine if the first time and date of the picture of the offender's face, the second time and date of the picture of the identification card are substantially the same; and
    a registration token to be sent to the app if the offender and a person in the picture of the identification card are substantially the same, and if the first time and date of the picture of the offender's face, the second time and date of the picture of the identification card are substantially the same.

2. The system according to claim 1, further comprising a not registered message configured to
    be sent to the app if at least one of an outcome of the image comparison algorithm is negative, or if an outcome of the location comparison algorithm is negative, or if an outcome of the time comparison is negative.

3. The system according to claim 1, wherein the system is configured to not send the registration token, if at least one of an outcome of the image comparison algorithm is negative, or if an outcome of the location comparison algorithm is negative, or if an outcome of the time comparison is negative.

4. The system according to claim 1, further comprising a verification system configured to:
    receive and store an initial secondary identifier at a first time;
    receive a second secondary identifier at a second time;
    compare the second secondary identifier to the initial secondary identifier;
    determine if the second secondary identifier and the initial secondary identifier are substantially the same; and
    renew the registration token if the second secondary identifier and the initial secondary identifier are substantially the same.

5. The system according to claim 4, wherein the secondary identifier is an image of a retina of an offender's eye captured by the camera.

6. The system according to claim 4, wherein the secondary identifier is at least one fingerprint of the offender captured by the device.

7. The system according to claim 4, wherein the secondary identifier is a voice pattern generated by the offender and captured by a microphone on the device.

8. The system according to claim 1, further comprising an interface between the identification engine and a third-party server, wherein the interface is configured to send offender parameters from the third-party server and to receive results from the identification engine.

9. The system according to claim 1, further comprising an interface between the verification and a third-party server, wherein the interface is configured to notify the third-party server that the registration token has been sent to the offender.

10. The system according to claim 4, further comprising an interface between the verification and a third-party server, wherein the interface is configured to notify the third-party server that a renewal of the registration token has been sent to the offender.

11. The system according to claim 1, further comprising an offender profile comprising the offender's name and at least one piece of data from the identification card.

12. The system according to claim 11, wherein the at least one piece of data comprises at least one of a legal name, an address, a birthdate, a gender, and a picture of the offender.

13. The system according to claim 11, wherein the verification engine is configured to collect text from the identification card, convert the text into the at least one piece of data and enter the at least one piece of data into the offender profile.

14. The system according to claim 11, wherein the offender profile comprises the identification data from the device.

15. A method for registering and monitoring a criminal offender over a network, the method comprising;
    generating an image of a face of an offender at a first location with a device comprising a clock and a GPS;
    tagging the image with GPS coordinates of the first location;
    tagging the image with a time and a date of the generating of the image;
    generating an image of an identification card comprising a picture of the offender at a second location;
    tagging the image of the identification card with GPS coordinates of the second location;

tagging the image of the identification card with a time and date of the generating of the image of the identification card;
comparing the image of the face and the image of the picture of the offender;
determining the likelihood that the image of the face and the image of the picture of the offender are substantially the same;
determining if the GPS coordinates of the first location and the GPS coordinates of the second location are substantially the same;
determining if the time and date of the generating the image of the face and the time and date of the generating the image of the identification card are within a defined time window; retrieving device identification data from the device;
tagging the image with the device identification data of the device generating the image of the face;
tagging the image of the identification card with the device identification data of the device generating the image of the identification card;
determining if the device identification data of the device generating the image of the face and the device identification data of the device generating the image of the identification card are the same; and
generating a registration token, if the image of the face and the image of the picture of the offender are substantially the same, if the GPS coordinates of the first location and the GPS coordinates of the second location are substantially the same, if the time and date of the generating the image of the face and the time and date of the generating the image of the identification card are within the defined time window, and if the device identification data of the device generating the image of face and the device identification data of the device generating the image of the identification card are the same.

16. The method according to claim 15, further comprising collecting data comprising at least one of a name, an address, a birthdate, and a gender from the image of the identification card and connecting the data to a offender profile.

17. The method according to claim 16, further comprising the steps of:
comparing the data to a database;
determining if the database identifies a defined null value; and
preventing the generating the registration token if the null value is identified.

18. The method according to claim 15, further comprising the steps of:
scanning the image of the identification card for a hologram;
comparing the hologram to a standard from a database;
determining if the identification card is fraudulent; and
preventing the generating of the registration token if the identification card is fraudulent.

19. The method according to claim 15, further comprising:
receiving and storing an initial secondary identifier after the generating the registration token;
requesting offender to input a secondary identifier at a later time;
receiving the secondary identifier from the offender;
comparing the secondary identifier to the initial secondary identifier;
determining if the secondary identifier and the initial secondary identifier are substantially the same; and
renewing the registration token if the secondary identifier and the initial secondary identifier are substantially the same.

20. The method according to claim 19, wherein the secondary identifier is one of:
a voice pattern generated by the offender and captured by a microphone on the device;
an image of a retina of an offender's eye captured by the device;
at least one fingerprint of the offender captured by the device;
a palm scan of the offender captured by the device;
a photo of the offender captured by the device;
a RFID tag tethered to the device; and
a password.

* * * * *